United States Patent
Garcia et al.

(10) Patent No.: US 12,084,684 B2
(45) Date of Patent: Sep. 10, 2024

(54) FRIZZLED SPECIFIC WNT AGONISTS AND ANTAGONISTS

(71) Applicants: The Board of Trustees of the Leland Stanford Junior University, Stanford, CA (US); UNIVERSITY OF WASHINGTON, Seattle, WA (US)

(72) Inventors: Kenan Christopher Garcia, Menlo Park, CA (US); Yi Miao, Palo Alto, CA (US); David Baker, Seattle, WA (US); Keunwan Park, Gangwon-do (KR); Luke Dang, Carnation, WA (US)

(73) Assignees: The Board of Trustees of the Leland Stanford Junior University; UNIVERSITY OF WASHINGTON, Seattle, WA (US)

( * ) Notice: Subject to any disclaimer, the term of this patent is extended or adjusted under 35 U.S.C. 154(b) by 651 days.

(21) Appl. No.: 17/259,508

(22) PCT Filed: Jul. 15, 2019

(86) PCT No.: PCT/US2019/041852
§ 371 (c)(1),
(2) Date: Jan. 11, 2021

(87) PCT Pub. No.: WO2020/018445
PCT Pub. Date: Jan. 23, 2020

(65) Prior Publication Data
US 2021/0317413 A1 Oct. 14, 2021

Related U.S. Application Data

(60) Provisional application No. 62/698,576, filed on Jul. 16, 2018.

(51) Int. Cl.
*C12N 5/0775* (2010.01)
*C07K 14/47* (2006.01)
*C12N 5/071* (2010.01)

(52) U.S. Cl.
CPC ........ *C12N 5/0662* (2013.01); *C07K 14/4703* (2013.01); *C07K 14/4705* (2013.01); *C12N 5/0697* (2013.01); *C07K 2319/74* (2013.01); *C12N 2501/415* (2013.01)

(58) Field of Classification Search
CPC .... C12N 5/0662; C12N 5/0697; C12N 14/47; C07K 14/4703; C07K 14/4705
USPC ................................. 435/320, 455; 530/387
See application file for complete search history.

(56) References Cited

U.S. PATENT DOCUMENTS

2014/0200179 A1 7/2014 Garcia
2017/0349659 A1 12/2017 Garcia et al.
2018/0137234 A1 5/2018 Baker et al.

FOREIGN PATENT DOCUMENTS

WO WO2016040895 A1 3/2016

OTHER PUBLICATIONS

Izumi et al., "Design of Peptide-based Inhibitors for Human Immunodeficiency Virus Type 1 Strains Resistant to T-20". The Journal of Biological Chemistry. Feb. 20, 2009. (284):8, 4914-4920. (Year: 2009).*
Li et al., "Ankyrin repeat: a unique motif mediating protein-protein interactions". Biochemistry. Dec. 26, 2006 ;45(51):15168-15178. (Year: 2006).*
Chen et al., "Fusion Protein Linkers: Property, Design and Functionality". Adv Drug Deliv Rev. Oct. 15, 2013; 65(10): 1357-1369 (Year: 2013).*
Database Geneseq [Online] (2018) "Self-assembling polypetide prepratin related Ank1, SEQ 5." Retrieved from EBI accession No. GSP:BFH30514.
Janda et al., (2017) "Surrogate Wnt agonists that phenocopy canonical Wnt and beta-catenin signalling", Nature, vol. 545, No. 7653, pp. 234-237.
Dang et al. (2019) "Receptor subtype discrimination using extensive shape complementary designed interfaces". Nature Structural & Molecular Biology. Jun. 2019, vol. 26, No. 6; pp. 407-414.

* cited by examiner

*Primary Examiner* — Anne Marie S Wehbe
*Assistant Examiner* — Hanan Isam Abuzeineh
(74) *Attorney, Agent, or Firm* — Pamela J. Sherwood; Bozicevic, Field & Francis LLP

(57) ABSTRACT

Wnt signaling antagonist and agonist compositions and methods for their use are provided.

13 Claims, 9 Drawing Sheets

Specification includes a Sequence Listing.

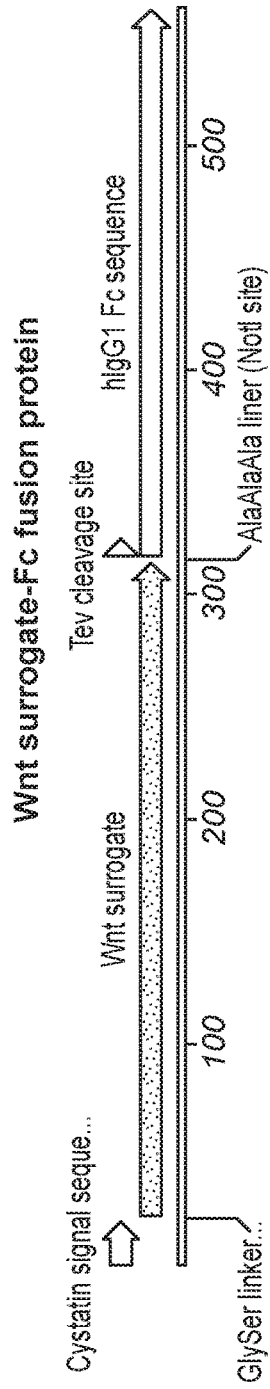

FIG. 8

Wnt surrogate-Fc fusion protein

1-20 Cystatin signal sequence
MARPLCTLLLIMATLAGALA 21-22 GlySer linker (BamHI-site)
GS 23-314 Wnt agonist sequence
SELGTRLIRAALDGNKDRVKDLIENGADVNASLMSGATPLHAAAMNGHKEVVKLLISKGADVNAQSVAG
STPLDAAAFSGHKEVVKLLISKGADNGHKEVVKLLISKGADVNAKADHGMTP
LHFAAQRGHKEVVKLLISKGADLNTSAKDGATPLDMARESGNEEVVKLLEKQLEGSGGSGSGKMYHT
KGQEGSVCLRSSDCASGLCCARHFWSKICKPVLKEGQVCTKHRRKGSHGLEIFQRCYCGEGLSCRIQKDHH
QASNSSRLHTCQRH 315-317 AlaAlaALa linker (NotI site)
AAA 318-325 Te cleavage site
ENLYFQGS 326-561 hFc tag
SEPKSCDKTHTCPPCPAPELLGGPSVFLFPPKPKDTLMISRTPEVTCVVVDVSHEDPEVKFNWYVDGVEVH
NAKTKPREEQYNSTYRVVSVLTVLHQDWLNGKEYKCKVSNKALPAPIEKTISKAKGQPREPQVYTLPPSRD
ELTKNQVSLTCLVKGFYPSDIAVEWESNGQPENNYKTTPPVLDSDGSFFLYSKLTVDKSRWQQGNVFSCSV
MHEALHNHYTQKSLSLSPGKAA

FRIZZLED SPECIFIC WNT AGONISTS AND ANTAGONISTS

CROSS REFERENCE

This application claims the benefit of U.S. Provisional Application No. 62/698,576, filed Jul. 16, 2018, which is incorporated herein by reference in its entirety.

BACKGROUND

Wnts (Wingless and Int-1) are central mediators of vertebrate and invertebrate development, due to their influences on cell proliferation, differentiation, and migration. Wnts act through activation of cell surface receptors on responder cells which activate at least three different signaling pathways including the "canonical" β-catenin pathway, and the "non-canonical" planar cell polarity (PCP) and $Cas^{2+}$ pathways.

Wnt/β-catenin signal transduction results in the cytoplasmic protein β-catenin entering the nucleus to modulate transcription. When the pathway is not activated, β-catenin is subject to a cycle of continual synthesis and destruction by the β-catenin destruction complex, comprised of the scaffold proteins Axin and APC and the kinases GSK3 and casein kinase 1 (CK1). Wnt signaling removes APC from the complex and relocalizes the other components to the plasma membrane via the adaptor Dsh, thus stabilizing β-catenin which enters the nucleus to mediate transcription.

The seven-pass transmembrane receptor Frizzled (Fz) is critical for nearly all Wnt signaling, and the N-terminal Fz cysteine rich domain (CRD) serves as the Wnt binding domain. In addition to Fz, the Wnt/β-catenin pathway requires the Low-density lipoprotein receptor related proteins 5 and 6 (Lrp5/6) to serve as co-receptors. LRP5 and LRP6 are functionally redundant single-pass transmembrane receptors. Biochemical studies of LRP6 indicate that different Wnts may bind to different extracellular domains of the LRP5/6 protein. The LRP6 extracellular domain contains four repeating sequences of β-propeller and epidermal growth factor-like (βP-E) domains. The crystal structures of the extracellular LRP6 regions indicate that the βP-E repeats represent two discrete, compact, rigid structures, each containing two βP-E pairs. Wnt9b binds the first two βP-E repeats on the extracellular domain of LRP6, whereas Wnt3a binds the last two βP-E domains. Binding of Wnt ligands to Fz and LRP5/6 results in the production of phosphatidylinositol (4,5)-bisphosphate (PIP2). Increased PIP2 induces oligomerization and clustering of LRP5/6. Increased PIP2 induces recruitment of Axin to LRP5/6. This recruitment may be due, in part, to the action of Amer1/WTX (APC membrane recruitment 1 or Wilms tumor gene on the X chromosome), a tumor suppressor mutated in Wilms' tumor that binds to Axin, CK1γ, and GSK3. Amer1/WTX is recruited to the plasma membrane in a PIP2-dependent manner.

The development of pharmaceutically active Wnt agonist and antagonists that are water soluble is therefore of great interest.

SUMMARY

Wnt is a lipidated protein that is difficult to express in a recombinant form. However, a number of in vitro cell culture systems, particularly those comprising stem cells, such as organoid cultures, may require the presence of Wnt, or molecules that act as Wnt signaling agonists. Provided herein are engineered proteins that act as Wnt signaling agonists or antagonists, which are readily expressed in conventional recombinant systems, and can be used in culture media to provide Wnt signaling agonist or antagonist activity. The engineered proteins are water soluble and bind with high affinity to frizzled (Fzd) proteins. A benefit of the proteins disclosed herein is their selectivity for binding to frizzled sub-types.

In one embodiment, engineered Wnt signaling antagonist DFBs proteins are provided. These proteins are exemplified by the sequences set forth in SEQ ID NO:1-4. The proteins were engineered from an ankyrin-repeat (ANK) based protein scaffold by amino acid substitutions and selections to provide for high affinity binding to selected Fzd proteins. The polypeptide binds one or more human Fzd proteins at high affinity, e.g. a Kd of less than about $1\times10^{-7}$ M, less than about $1\times10^{-8}$ M, less than about $1\times10^{-9}$ M, or less than about $1\times10^{-10}$ M. Fzd binding domain can also be affinity selected to enhance binding to a desired Fzd protein or plurality of Fzd proteins, e.g. to provide tissue selectivity. In some embodiments the Fzd binding domain binds to one, two, three, four, five or more different frizzled proteins, e.g. one or more of human frizzled proteins Fz1, Fz2, Fz3, Fz4, Fz5, Fz6, Fz7, Fz8, Fz9, Fz10. The frizzled binding domain can have a specificity for the one or more desired frizzled protein of at least 10-fold, 25-fold, 50-fold, 100-fold, 200-fold or more relative to other frizzled proteins.

In another embodiment, engineered Wnt signaling agonist proteins are provided, which are comprised of a Wnt signaling antagonist, e.g. comprising a sequence of any of SEQ ID NO:1-4, joined to an Lrp-binding domain. These proteins are exemplified by the sequences set forth in SEQ ID NO:5-8. The Wnt signaling agonist molecule is therefore comprised of separate or contiguous binding domains or elements for Fzd, and for Lrp5/6. The Fzd binding domain/element and the Lrp5/6 binding domain/element may be directly fused, or may be separated by a linker, e.g. a polypeptide linker, or a non-peptidic linker, etc. Where the linker is a peptide linker, it may be from about 1, 2, 3, 4, 5, 6, 7, 8, 9, 10, 11, 12, 13, 14, 15, 16, 17, 18, 19, 20 21, 22, 23, 24, 25, 26, 27, 28, 29, 30 or more amino acids in length, and is of sufficient length and amino acid composition to enforce the distance between binding domains. In some embodiments the linker comprises or consists of one or more glycine and/or serine residues. The Lrp5/6 binding domain or element binds Lrp5/6 at high affinity, e.g. a $K_D$ of less than about $1\times10^{-7}$ M, less than about $1\times10^{-8}$ M, less than about $1\times10^{-9}$ M, less than about $1\times10^{-10}$ M. Suitable Lrp5/6 binding domains include DKK1, DKK2, DKK3, DKK4; and the like. In certain embodiments the Lrp5/6 binding domain is the c-terminal portion of DKK1.

A Wnt signaling agonist or antagonist described herein can be multimerized, e.g. through an Fc domain, by concatenation, coiled coils, polypeptide zippers, biotin/avidin or streptavidin multimerization, and the like. The Wnt signaling agonist can also be joined to a moiety such as PEG, Fc, etc. as known in the art to enhance stability in vivo.

Compositions of interest include, without limitation, an effective dose of an agonist or antagonist described herein in culture media, or a pharmaceutically acceptable excipient. Such compositions may comprise additional agents, e.g. adjuvants, additional growth factors, and the like. Wnt signaling agonists or antagonists described herein may be produced synthetically; by various suitable recombinant methods, and the like, as known in the art. In addition, a benefit of the water soluble polypeptides provided herein is the lack of a requirement for formulation additives, e.g. lipids, detergents, etc. that might limit their therapeutic utility.

In some aspects of the invention, a method is provided for altering, activating, increasing or enhancing Wnt signaling in a cell, including without limitation a cell grown in medium in vitro, e.g. an organoid culture. In such methods, a cell expressing a frizzled receptor is contacted with a concentration of a Wnt signaling agonist that is effective to increase signaling, e.g. to increase signaling by 25%, 50%, 75%, 90%, 95%, or more, relative to the signaling in the absence of the Wnt signaling agonist. Such signaling activation may induce proliferation of the targeted cell, which cells include without limitation organoids, stem cells, etc.

BRIEF DESCRIPTION OF THE DRAWINGS

The invention is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity. Included in the drawings are the following figures.

(FIG. 1A) ANK12 yeast titration with individual Fzd CRD. (FIG. 1B) SPR results of ANK12 to Fzd4, 7 and 8.

(FIG. 5A) Activity of DFBs agonists on HEK293T cell line with Fzd1/2/415/7/8 knockout. (FIG. 5B) Activity of agonists against HEK293T cell line with Fzd1/2/4/5/7/8 knockout with transfected Fzd4 receptor. (FIG. 5C) Activity of agonists against HEK293T cell line with Fzd1/2/4/5/7/8 knockout with transfected Fzd7 receptor. (FIG. 5D) Activity of agonists against HEK293T cell line with Fzd1/2/4/5/7/8 knockout with transfected Fzd8 receptor. Going from left to right, starting concentrations are 100 nM with 2-fold dilution to 0.39 nM.

FIG. 8. A schematic and sequence of an exemplary expression construct, in which the Wnt signaling agonist is expressed with a cystatin signal sequence, a linker, and an Fc tag joined by a cleavable linker. The complete construct is shown as SEQ ID NO:14. The coding sequence is provided as SEQ ID NO:15. The mature protein comprises the sequence of SEQ ID NO:5.

DETAILED DESCRIPTION OF THE INVENTION

Figure 1A:
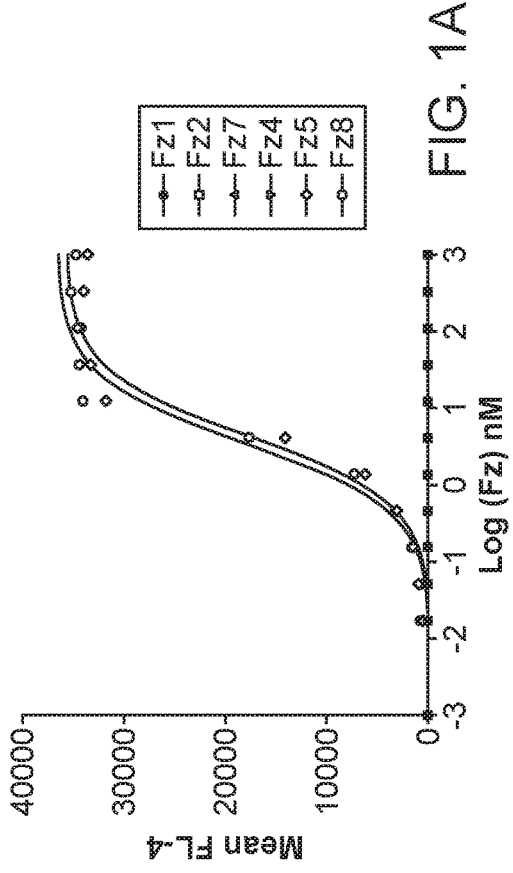
FIG. 1A-1B.

Before the present methods and compositions are described, it is to be understood that this invention is not limited to particular method or composition described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited. It is understood that the present disclosure supersedes any disclosure of an incorporated publication to the extent there is a contradiction.

It must be noted that as used herein and in the appended claims, the singular forms "a", "an", and "the" include plural referents unless the context clearly dictates otherwise. Thus, for example, reference to "a cell" includes a plurality of such cells and reference to "the peptide" includes reference to one or more peptides and equivalents thereof, e.g. polypeptides, known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

By "comprising" it is meant that the recited elements are required in the composition/method/kit, but other elements may be included to form the composition/method/kit etc. within the scope of the claim. For example, a composition comprising a Wnt agonist or antagonist described herein is a composition that may comprise other elements in addition to Wnt agonist or antagonist described herein, e.g. functional moieties such as polypeptides, small molecules, or nucleic acids bound, e.g. covalently bound, to the Wnt agonist or antagonist described herein; agents that promote the stability, agents that promote solubility, adjuvants, etc. as will be readily understood in the art, with the exception of elements that are encompassed by any negative provisos.

By "consisting essentially of", it is meant a limitation of the scope of composition or method described to the specified materials or steps that do not materially affect the basic and novel characteristic(s) of the subject invention. For example, a Wnt agonist or antagonist "consisting essentially of" a disclosed sequence has the amino acid sequence of the disclosed sequence plus or minus about 5 amino acid residues at the boundaries of the sequence based upon the sequence from which it was derived, e.g. about 5 residues, 4 residues, 3 residues, 2 residues or about 1 residue less than the recited bounding amino acid residue, or about 1 residue, 2 residues, 3 residues, 4 residues, or 5 residues more than the recited bounding amino acid residue.

By "consisting of", it is meant the exclusion from the composition, method, or kit of any element, step, or ingredient not specified in the claim. For example, a Wnt agonist or antagonist "consisting of" a disclosed sequence consists only of the disclosed amino acid sequence.

General methods in molecular and cellular biochemistry can be found in such standard textbooks as Molecular Cloning: A Laboratory Manual, 3rd Ed. (Sambrook et al., CSH Laboratory Press 2001); Short Protocols in Molecular Biology, 4th Ed. (Ausubel et al. eds., John Wiley & Sons 1999); Protein Methods (Bollag et al., John Wiley & Sons 1996); Nonviral Vectors for Gene Therapy (Wagner et al. eds., Academic Press 1999); Viral Vectors (Kaplift & Loewy eds., Academic Press 1995); Immunology Methods Manual (I. Lefkovits ed., Academic Press 1997); and Cell and Tissue Culture: Laboratory Procedures in Biotechnology (Doyle & Griffiths, John Wiley & Sons 1998), the disclosures of which are incorporated herein by reference. Reagents, cloning vectors, and kits for genetic manipulation referred to in this disclosure are available from commercial vendors such as BioRad, Stratagene, Invitrogen, Sigma-Aldrich, and ClonTech.

Compositions

Wnt signaling agonist or antagonist proteins and methods for their use are provided. These and other objects, advantages, and features of the invention will become apparent to those persons skilled in the art upon reading the details of the compositions and methods as more fully described below.

Wnt signaling agonist or antagonist proteins of the present invention are biologically active in binding to a cognate Frizzled receptor, resulting in activation or inhibition of Wnt signaling. The term "Wnt signaling agonist activity" refers to the ability of an agonist to mimic the effect or activity of a Wnt protein binding to a frizzled protein and Lrp, thereby activating the Wnt signaling pathway. The term "Wnt signaling antagonist activity" refers to the ability of an antagonist to reduce or otherwise block Wnt protein binding to a frizzled protein, thereby reducing activity of the Wnt signaling pathway.

The ability of the engineered proteins to mimic or inhibit the activity of Wnt can be confirmed by a number of assays. The engineered proteins typically initiate a reaction or activity that is similar to or the same as that initiated by the receptor's natural ligand. In particular, agonists of the invention enhance the canonical Wnt/β-catenin signaling pathway while antagonists inhibit the pathway. As used herein, the term "enhances" refers to a measurable increase in the level of Wnt/β-catenin signaling compared with the level in the absence of an agonist of the invention.

Various methods are known in the art for measuring the level of canonical Wnt/β-catenin signaling. These include, but are not limited to assays that measure: Wnt/β-catenin target gene expression; TCF reporter gene expression; beta-catenin stabilization; LRP phosphorylation; Axin translocation from cytoplasm to cell membrane and binding to LRP. The canonical Wnt/β-catenin signaling pathway ultimately leads to changes in gene expression through the transcription factors TCF7, TCF7L1, TCF7L2 and LEF. The transcriptional response to Wnt activation has been characterized in a number of cells and tissues. As such, global transcriptional profiling by methods well known in the art can be used to assess Wnt/β-catenin signaling activation.

Changes in Wnt-responsive gene expression are generally mediated by TCF and LEF transcription factors. A TCF reporter assay assesses changes in the transcription of TCF/LEF controlled genes to determine the level of Wnt/.beta.-catenin signaling. A TCF reporter assay was first described by Korinek, V. et al., 1997. Also known as TOP/FOP this method involves the use of three copies of the optimal TCF motif CCTTTGATC, or three copies of the mutant motif CCTTTGGCC, upstream of a minimal c-Fos promoter driving luciferase expression (pTOPFLASH and pFOPFLASH, respectively) to determine the transactivational activity of endogenous β-catenin/TCF4. A higher ratio of these two reporter activities (TOP/FOP) indicates higher β-catenin/TCF4 activity.

Various other reporter transgenes that respond to Wnt signals exist intact in animals and therefore, effectively reflect endogenous Wnt signaling. These reporters are based on a multimerized TCF binding site, which drives expression of LacZ or GFP, which are readily detectable by methods known in the art. These reporter genes include: TOP-GAL, BAT-GAL, ins-TOPEGFP, ins-TOPGAL, LEF-EGFP, Axin2-LacZ, Axin2-d2EGFP, Lgr5tm1(cre/ERT2), TOPdGFP.

The recruitment of dephosphorylated β-catenin to the membrane, stabilisation and phosphorylation status of β-catenin and translocation of β-catenin to the nucleus (Klapholz-Brown Z et al., PLoS One. 2(9) e945, 2007) in some cases mediated by complex formation with TCF transcription factors and TNIK are key steps in the Wnt signaling pathway. Stabilisation is mediated by Disheveled family proteins that inhibit the "destruction" complex so that degradation of intracellular β-catenin is reduced, and translocation of β-catenin to the nucleus follows thereafter. Therefore, measuring the level and location of β-catenin in a cell is a good reflection of the level of Wnt/β-catenin signaling. A non-limiting example of such an assay is the "BioImage β-Catenin Redistribution Assay" (Thermo Scientific) which provides recombinant U2OS cells that stably express human β-catenin fused to the C-terminus of enhanced green fluorescent protein (EGFP). Imaging and analysis is performed with a fluorescence microscope or HCS platform allowing the levels and distribution of EGFP-β-catenin to be visualized.

Another way, in which the destruction complex is inhibited, is by removal of Axin by recruitment of Axin to the cytoplasmic tail of the Wnt co-receptor LRP. Axin has been shown to bind preferentially to a phosphorylated form of the LRP tail. Visualisation of Axin translocation, for example with a GFP-Axin fusion protein, is therefore another method for assessing levels of Wnt/β-catenin signaling.

In certain embodiments, the agonist or antagonist of the invention alter β-catenin signaling by at least 30%, 35%, 40%, 45%, 50%, 60%, 70%, 75%, 80%, 85%, 90%, 95%, 100%, 110%, 150%, 200%, 250%, 300%, 400% or 500% compared to the β-catenin signaling induced by a neutral substance or negative control as measured in an assay described above, for example as measured in the TOPFlash assay. A negative control may be included in these assays.

"Wnt gene product" or "Wnt polypeptide" when used herein encompass native sequence Wnt polypeptides, Wnt polypeptide variants, Wnt polypeptide fragments and chimeric Wnt polypeptides. In particular embodiments, a Wnt polypeptide is a native human full length mature Wnt protein. For example, human native sequence Wnt proteins of interest in the present application include the following: Wnt-1 (GenBank Accession No. NM_005430); Wnt-2 (GenBank Accession No. NM_003391); Wnt-2B (Wnt-13) (GenBank Accession No. NM_004185 (isoform 1), NM_024494.2 (isoform 2)), Wnt-3 (RefSeq.: NM_030753), Wnt3a (GenBank Accession No. NM_033131), Wnt-4 (GenBank Accession No. NM_030761), Wnt-5A (GenBank Accession No. NM_003392), Wnt-5B (GenBank Accession No. NM_032642), Wnt-6 (GenBank Accession No. NM_006522), Wnt-7A (GenBank Accession No. NM_004625), Wnt-7B (GenBank Accession No. NM_058238), Wnt-8A (GenBank Accession No. NM_058244), Wnt-8B (GenBank Accession No. NM_003393), Wnt-9A (Wnt-14) (GenBank Accession No. NM_003395), Wnt-9B (Wnt-15) (GenBank Accession No. NM_003396), Wnt-10A (GenBank Accession No. NM_025216), Wnt-10B (GenBank Accession No. NM_003394), Wnt-11 (GenBank Accession No. NM_004626), Wnt-16 (GenBank Accession No. NM_016087)). Although each member has varying degrees of sequence identity with the family, all encode small (i.e., 39-46 kD), acylated, palmitoylated, secreted glycoproteins that contain 23-24 conserved cysteine residues whose spacing is highly conserved (McMahon, A P et al., Trends Genet. 1992; 8: 236-242; Miller, J R. Genome Biol. 2002; 3(1): 3001.1-3001.15).

"Wnt protein signaling" or "Wnt signaling" is used herein to refer to the mechanism by which a biologically active Wnt exerts its effects upon a cell to modulate a cell's activity. Wnt proteins modulate cell activity by binding to Wnt receptors, including proteins from the Frizzled (Fz) family of proteins, proteins from the ROR family of proteins, the proteins LRP5, LRP6 from the LRP family of proteins, the protein FRL1/crypto, and the protein Derailed/Ryk. Once activated by Wnt binding, the Wnt receptor(s) will activate one or more intracellular signaling cascades. These include the canonical Wnt signaling pathway; the Wnt/planar cell polarity (Wnt/PCP) pathway; the Wnt-calcium (Wnt/Ca$^{2+}$) pathway (Giles, R H et al. (2003) Biochim Biophys Acta 1653, 1-24; Peifer, M. et al. (1994) Development 120: 369-380; Papkoff, J. et al (1996) Mol. Cell Biol. 16: 2128-2134; Veeman, M. T. et al. (2003) Dev. Cell 5: 367-377); and other Wnt signaling pathways as is well known in the art. Activation of the canonical Wnt signaling pathway results in the inhibition of phosphorylation of the intracellular protein ß-catenin, leading to an accumulation of ß-catenin in the cytosol and its subsequent translocation to the nucleus where it interacts with transcription factors, e.g. TCF/LEF, to activate target genes. A "biologically active Wnt signaling agonist" is a Wnt signaling agonist composition that is able to specifically bind to a Fzd receptor and activate Wnt signaling when provided to a cell in vitro or in vivo, that is, when present in cell culture media, etc.

In certain embodiments, a Wnt signaling agonist or antagonist alters signaling of the canonical Wnt pathway by at least about 50%, about 75%, about 100%, about 150%, about 200%, about 300%, about 400%, about 5-fold, about 10-fold, and may increase or decrease signaling by 50-fold, 100-fold, 500-fold, or more, relative to the level of Wnt signaling in the absence of the protein.

The term "specific binding" refers to that binding which occurs between such paired species as enzyme/substrate, receptor/ligand, etc. which may be mediated by covalent or non-covalent interactions or a combination of covalent and non-covalent interactions. Accordingly, "specific binding" occurs between a paired species where there is interaction between the two which produces a bound complex. Methods known in the art may be used to determine the affinity of the interaction.

By "water soluble" it is meant a composition that is soluble in aqueous buffers in the absence of detergent, usually soluble at a concentration that provides a biologically effective dose of the polypeptide. Compositions that are water soluble form a substantially homogeneous composition that has a specific activity that is at least about 5% that of the starting material from which it was purified, usually at least about 10%, 20%, or 30% that of the starting material, more usually about 40%, 50%, or 60% that of the starting material, and may be about 50%, about 90% or greater. Engineered proteins compositions of the present invention typically form a substantially homogeneous aqueous solution at concentrations of at least 25 µM and higher, e.g. at least 25 µM, 40 µM, or 50 µM, usually at least 60 µM, 70 µM, 80 µM, or 90 µM, sometimes as much as 100 µM, 120 µM, or 150 µM. In other words, proteins of the present invention typically form a substantially homogeneous aqueous solution at concentrations of about 0.1 mg/ml, about 0.5 mg/ml, of about 1 mg/ml or more.

Fzd binding domain. The Fzd binding domain is an engineered protein as described herein and exemplified by the polypeptides of any of SEQ ID NO:1-4. The polypeptides bind to at least one Fzd protein at high affinity, e.g. a $K_D$ of less than about $1\times10^{-7}$ M, less than about $1\times10^{-8}$ M, less than about $1\times10^{-9}$ M, less than about $1\times10^{-10}$ M. Suitable Fzd binding domains are engineered Fzd binding proteins based on a DFBs scaffold; and the like. The Fzd binding domains have been affinity selected to enhance binding to a desired Fzd protein or plurality of Fzd proteins, e.g. to provide tissue selectivity. Methods of affinity selection for this purpose utilize one or more rounds of selection by introducing targeted amino acid changes and generating a library of candidate coding sequences, transforming a population of cells with the candidate coding sequence, e.g. into yeast cells, selecting (for example using paramagnetic microbeads) for the desired specificity. Typically multiple rounds of selection are performed, and the resulting vectors sequenced and used as the basis for protein engineering. The Fzd binding domain may bind to one, two, three, four, five or more different frizzled proteins, e.g. one or more of human frizzled proteins Fz1, Fz2, Fz3, Fz4, Fz5, Fz6, Fz7, Fz8, Fz9, Fz10.

Lrp5/6 binding domain. An Lrp5/6 may be selected from any domain that binds Lrp5 or Lrp6 at high affinity, e.g. with a $K_D$ of less than about $1\times10^{-7}$ M, less than about $1\times10^{-8}$ M, less than about $1\times10^{-9}$ M, less than about $1\times10^{-10}$ M.

"LRP", "LRP proteins" and "LRP receptors" is used herein to refer to proteins of the low density lipoprotein receptor-related protein family. These receptors are single-pass transmembrane proteins that bind and internalize ligands in the process of receptor-mediated endocytosis. LRP proteins LRP5 (GenBank Accession No. NM 002335.2) and LRP6 (GenBank Accession No. NM 002336.2) are included in the Wnt receptor complex.

Suitable Lrp5/6 binding domains include, without limitation, de novo designed Lrp5/6 binding proteins, antibody derived binding proteins, e.g. scFv, Fab, etc. and other portions of antibodies that specifically bind to one or more Fzd proteins; nanobody derived binding domains; knottin-based engineered scaffolds; naturally occurring Lrp5/6, including particularly limitation, DKK1, DKK2, DKK3, DKK4, sclerostin; Wise; fusions proteins comprising any of the above; derivatives of any of the above; variants of any of the above; and biologically active fragments of any of the above, and the like.

Members of the Dickkopf (Dkk) gene family (see Krupnik et al. (1999) Gene 238(2):301-13) include Dkk-1, Dkk-2, Dkk-3, and Dkk-4, and the Dkk-3 related protein Soggy (Sgy). hDkks 1-4 contain two distinct cysteine-rich domains in which the positions of 10 cysteine residues are highly conserved between family members. Exemplary sequences of human Dkk genes and proteins are publicly available, e.g. Genbank accession number NM_014419

(soggy-1); NM_014420 (DKK4); AF177394 (DKK-1); AF177395 (DKK-2); NM_015881 (DKK3); and NM_014421 (DKK2). In some embodiments of the invention, the Lrp6 binding moiety is a DKK1 peptide, including without limitation the C-terminal domain of human DKK1. The C-terminal domain may comprise the sequence (SEQ ID NO:12) KMYHTKGQEGSVCLRSSDCASGLCCA-RHFWSKICKPVLKEGQVCTKHRRKGSHGLEIFQRCY CGEGLSCRIQKDHHQASNSSRLHTCQRH (see Genbank accession number NP_036374) or a biologically active fragment thereof.

Binding of DKK proteins to LRP5/6 are discussed, for example in Brott and Sokol Mol. Cell. Biol. 22 (17), 6100-6110 (2002); and Li et al. J. Biol. Chem. 277 (8), 5977-5981 (2002), each herein specifically incorporated by reference. The corresponding region of human DKK2 (Genbank reference NP_055236) may comprise the sequence (SEQ ID NO:13) KMSHIKGHEGDPCLRSSDCIEGFCCA-RHFWTKICKPVLHQGEVCTKQRKKGSHGLE-IFQRCDC AKGLSCKVWKDATYSSKARLHVCQK or a biologically active fragment thereof.

Variants. The polypeptides provided herein may be modified to generate derivatives, variants, and biologically active fragments. A "variant" polypeptide means a biologically active polypeptide as defined below having less than 100% sequence identity with a provided sequence. Such variants include polypeptides comprising one or more amino acid modifications, e.g., insertions, deletions or substitutions, as compared to the provided sequence, e.g., wherein one or more amino acid residues are added at the N- or C-terminus of, or within, the native sequence; from about one to forty amino acid residues are deleted, and optionally substituted by one or more amino acid residues; and derivatives of the above polypeptides, wherein an amino acid residue has been covalently modified so that the resulting product has a non-naturally occurring amino acid. Ordinarily, a biologically active variant will have an amino acid sequence having at least about 90% amino acid sequence identity with a native sequence polypeptide, preferably at least about 95%, more preferably at least about 99%.

A "functional derivative" of a sequence is a compound having a qualitative biological property in common with an initial sequence. "Functional derivatives" include, but are not limited to, fragments of a sequence and derivatives of a sequence, provided that they have a biological activity in common. The term "derivative" encompasses both amino acid sequence variants of polypeptide and covalent modifications thereof.

Wnt signaling agonists or antagonists for use in the subject compositions and methods may be modified using ordinary molecular biological techniques and synthetic chemistry so as to improve their resistance to proteolytic degradation or to optimize solubility properties or to render them more suitable as a therapeutic agent. Analogs of such polypeptides include those containing residues other than naturally occurring L-amino acids, e.g. D-amino acids or non-naturally occurring synthetic amino acids. D-amino acids may be substituted for some or all of the amino acid residues.

The Wnt signaling agonist or antagonists may be prepared by in vitro synthesis, using conventional methods as known in the art. Various commercial synthetic apparatuses are available, for example, automated synthesizers by Applied Biosystems, Inc., Beckman, etc. By using synthesizers, naturally occurring amino acids may be substituted with unnatural amino acids. The particular sequence and the manner of preparation will be determined by convenience, economics, purity required, and the like. If desired, various groups may be introduced into the peptide during synthesis or during expression, which allow for linking to other molecules or to a surface. Thus cysteines can be used to make thioethers, histidines for linking to a metal ion complex, carboxyl groups for forming amides or esters, amino groups for forming amides, and the like.

A Wnt signaling agonist or antagonist may be fused or bonded to an additional polypeptide sequence. Examples include signal sequences for secretion of the polypeptides, immunoadhesins, which combine a Wnt signaling agonist or antagonist with an immunoglobulin sequence, particularly an Fc sequence, and epitope tagged polypeptides, which comprise a native inhibitors polypeptide or portion thereof fused to a "tag polypeptide". The tag polypeptide has enough residues to provide an epitope against which an antibody can be made, yet is short enough such that it does not interfere with biological activity of the original polypeptide. Suitable tag polypeptides generally have at least six amino acid residues and usually between about 6-60 amino acid residues. The Wnt agonist or antagonist may also be fused or combined in a formulation, or co-administered with an agent that enhances Wnt activity, e.g. R-spondin 1, R-spondin 2, anti-sclerosin antibody, etc.

Linker. The Fzd binding sequence and the Lrp5/6 binding sequence may be separated by a linker, e.g. a polypeptide linker, or a non-peptidic linker, etc. In some embodiments the linker is a rigid linker, in other embodiments the linker is a flexible linker. In some embodiments, the linker moiety is a peptide linker. In some embodiments, the peptide linker comprises 2 to 100 amino acids. In some embodiments, the peptide linker comprises 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 but no greater than 100 amino acids. In some embodiments, the peptide linker is between 5 to 75, 5 to 50, 5 to 25, 5 to 20, 5 to 15, 5 to 10 or 5 to 9 amino acids in length. Exemplary linkers include linear peptides having at least two amino acid residues such as Gly-Gly, Gly-Ala-Gly, Gly-Pro-Ala, Gly-Gly-Gly-Gly-Ser. Suitable linear peptides include poly glycine, polyserine, polyproline, polyalanine and oligopeptides consisting of alanyl and/or serinyl and/or prolinyl and/or glycyl amino acid residues. In some embodiments, the peptide linker comprises the amino acid sequence selected from the group consisting of $Gly_9$, $Glu_9$, $Ser_9$, $Gly_5$-Cys-$Pro_2$-Cys, $(Gly_4$-Ser$)_3$, Ser-Cys-Val-Pro-Leu-Met-Arg-Cys-Gly-Gly-Cys-Cys-Asn, Pro-Ser-Cys-Val-Pro-Leu-Met-Arg-Cys-Gly-Gly-Cys-Cys-Asn, Gly-Asp-Leu-Ile-Tyr-Arg-Asn-Gln-Lys, and $Gly_9$-Pro-Ser-Cys-Val-Pro-Leu-Met-Arg-Cys-Gly-Gly-Cys-Cys-Asn. In one embodiment a linker comprises the amino acid sequence GSTSGSGKSSEGKG, or (GGGGS)n, where n is 1, 2, 3, 4, 5, etc.; however many such linkers are known and used in the art and may serve this purpose.

The term "cell culture" or "culture" means the maintenance of cells in an artificial, in vitro environment. It is to be understood, however, that the term "cell culture" is a generic term and may be used to encompass the cultivation not only of individual cells, but also of tissues or organs.

The term "culture system" is used herein to refer to the culture conditions in which the subject explants are grown that promote prolonged tissue expansion with proliferation, multilineage differentiation and recapitulation of cellular and tissue ultrastructure.

By "container" is meant a glass, plastic, or metal vessel that can provide an aseptic environment for culturing cells.

Organoid Culture. Organoids are in-vitro derived 3-dimensional cell aggregates derived from primary tissue or stem cells that are capable of self-renewal, self-organization and exhibit organ functionality. Organoids provide a 3-dimensional model system that recapitulates body processes and functions from the molecular to whole organism level. 3D cell culture models are a more accurate representation of the natural environment experienced by cells in the living organism as opposed to growing cells on 2D flat surfaces.

Generally organoids harbor small population of self-renewing stem cells that can differentiate into cells of all major cell lineages, with similar frequency as in physiological condition. For example, organoids may be generated either from primary tissues or pluripotent stem cells (induced pluripotent stem cells (iPSC) or embryonic stem cells (ESCs)) by providing appropriate physical and biochemical cue. As such, organoids are biologically relevant to any model system and are amenable to manipulate niche components and gene sequence. However, the presence of the stem cells requires that suitable growth factors also be present, which may include Wnt proteins. The difficulty in producing Wnt protein for this purpose is addressed by the use of the engineered molecules, described herein, particularly Wnt agonist polypeptides, described herein.

Organoid cultures are useful as in vitro model systems, to study processes including tumorigenesis, infection, gene correction, drug toxicity and efficacy testing, etc. Organoids may also provide cells for regenerative medicine. Organoids are also useful in personalized medicine applications, for example organoids derived from adult stem cell of individual patients allows ex-vivo testing of drug response and treatment options.

See, for example, Yin et al. (2016) Cell Stem Cell 18, 25-38; Lancaster and Knoblich (2014) Science 345, 1247125; Clevers (2016) Cell 165, 1586-1597; Eiraku and Sasai (2012) Curr. Opin. Neurobiol. 22, 768-777; Nakano et al. (2012) Cell Stem Cell 10, 771-785; McCracken et al. (2014) Nature 516, 400-404; Wong et al. (2012) Nat. Biotechnol. 30, 876-882; Huang et al. (2014) Nat. Biotechnol. 32, 84-91; Takebe et al. (2013) Nature 499, 481-484; Takasato et al. (2015) Nature 526, 564-568; Sato and Clevers (2013) Science 340, 1190-1194; Huch et al. (2015) Cell 160, 299-312; Unnemann et al. (2015) Dev. Camb. Engl. 142, 3239-3251; Boj et al. (2015) Cell 160, 324-338; Ciancanelli et al. (2015) Science 348, 448-453; Qian, et al. (2016) Cell 165, 1238-1254; Spence et al. (2011) Nature 470, 105-109.

The terms "stem cell" as used herein, refer to a cell that has the property of self-renewal and has the developmental potential to differentiate into multiple cell types. A stem cell is capable of proliferation and giving rise to more such stem cells while maintaining its developmental potential. Stem cells can divide asymmetrically, with one daughter cell retaining the developmental potential of the parent stem cell and the other daughter cell expressing some distinct other specific function, phenotype and/or developmental potential from the parent cell. The daughter cells themselves can be induced to proliferate and produce progeny that subsequently differentiate into one or more mature cell types, while also retaining one or more cells with parental developmental potential. A differentiated cell may derive from a multipotent cell, which itself is derived from a multipotent cell, and so on. While each of these multipotent cells may be considered stem cells, the range of cell types each such stem cell can give rise to, i.e., their developmental potential, can vary considerably. Alternatively, some of the stem cells in a population can divide symmetrically into two stem cells, known as stochastic differentiation, thus maintaining some stem cells in the population as a whole, while other cells in the population give rise to differentiated progeny only. Accordingly, the term "stem cell" refers to any subset of cells that have the developmental potential, under particular circumstances, to differentiate to a more specialized or differentiated phenotype, and which retain the capacity, under certain circumstances, to proliferate without substantially differentiating.

The term "somatic stem cell" is used herein to refer to any pluripotent or multipotent stem cell derived from non-embryonic tissue, including fetal, juvenile, and adult tissue. Natural somatic stem cells have been isolated from a wide variety of adult tissues including blood, bone marrow, brain, olfactory epithelium, skin, pancreas, skeletal muscle, and cardiac muscle. The term "progenitor cell" is used herein to refer to cells that are at an earlier stage along a developmental pathway or progression, relative to a cell which it can give rise to by differentiation. Often, progenitor cells have significant or very high proliferative potential. Progenitor cells can give rise to multiple distinct differentiated cell types, or to a single differentiated cell type, depending on the developmental pathway and on the environment in which the cells develop and differentiate.

Expression construct. In the present methods, a Wnt signaling agonist or antagonist, if a polypeptide, may be produced by recombinant methods. The nucleic acid encoding the Wnt agonist or antagonist can be inserted into a replicable vector for expression. Many such vectors are available. The vector components generally include, but are not limited to, one or more of the following: an origin of replication, one or more marker genes, an enhancer element, a promoter, and a transcription termination sequence. Exemplary coding sequences for a Wnt signaling agonist are provided as SEQ ID NO:9 and SEQ ID NO:10. Codon usage may be optimized for the desired host cell.

Expression vectors will contain a promoter that is recognized by the host organism and is operably linked to the Wnt agonist or antagonist coding sequence. Promoters are untranslated sequences located upstream (5') to the start codon of a structural gene (generally within about 100 to 1000 bp) that control the transcription and translation of particular nucleic acid sequence to which they are operably linked. Such promoters typically fall into two classes, inducible and constitutive. Inducible promoters are promoters that initiate increased levels of transcription from DNA under their control in response to some change in culture conditions, e.g., the presence or absence of a nutrient or a change in temperature.

Promoters suitable for use with prokaryotic hosts include the β-lactamase and lactose promoter systems, alkaline phosphatase, a tryptophan (trp) promoter system, and hybrid promoters such as the tac promoter. However, other known bacterial promoters are also suitable. Such nucleotide sequences have been published, thereby enabling a skilled worker operably to ligate them to a DNA coding sequence. Promoters for use in bacterial systems also will contain a Shine-Dalgarno (S.D.) sequence operably linked to the coding sequence.

Promoter sequences are known for eukaryotes. Examples of suitable promoting sequences for use with yeast hosts include the promoters for 3-phosphoglyceratekinase or other glycolytic enzymes, such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in EP 73,657. Yeast enhancers also are advantageously used with yeast promoters.

Transcription from vectors in mammalian host cells may be controlled, for example, by promoters obtained from the genomes of viruses such as polyoma virus, fowlpox virus, adenovirus (such as Adenovirus 2), bovine papilloma virus, avian sarcoma virus, cytomegalovirus, a retrovirus, hepatitis-B virus and most preferably Simian Virus 40 (SV40), from heterologous mammalian promoters, e.g., the actin promoter, PGK (phosphoglycerate kinase), or an immunoglobulin promoter, from heat-shock promoters, provided such promoters are compatible with the host cell systems. The early and late promoters of the SV40 virus are conveniently obtained as an SV40 restriction fragment that also contains the SV40 viral origin of replication. The immediate early promoter of the human cytomegalovirus is conveniently obtained as a HindIII E restriction fragment.

Transcription by higher eukaryotes is often increased by inserting an enhancer sequence into the vector. Enhancers are cis-acting elements of DNA, usually about from 10 to 300 bp, which act on a promoter to increase its transcription. Enhancers are relatively orientation and position independent, having been found 5' and 3' to the transcription unit, within an intron, as well as within the coding sequence itself. Many enhancer sequences are now known from mammalian genes (globin, elastase, albumin, α-fetoprotein, and insulin). Typically, however, one will use an enhancer from a eukaryotic cell virus. Examples include the SV40 enhancer on the late side of the replication origin, the cytomegalovirus early promoter enhancer, the polyoma enhancer on the late side of the replication origin, and adenovirus enhancers. The enhancer may be spliced into the expression vector at a position 5' or 3' to the coding sequence, but is preferably located at a site 5' from the promoter.

Expression vectors used in eukaryotic host cells (yeast, fungi, insect, plant, animal, human, or nucleated cells from other multicellular organisms) may also contain sequences necessary for the termination of transcription and for stabilizing the mRNA. Such sequences are commonly available from the 5' and, occasionally 3', untranslated regions of eukaryotic or viral DNAs or cDNAs.

Construction of suitable vectors containing one or more of the above-listed components employs standard techniques. Isolated plasmids or DNA fragments can be cleaved, tailored, and re-ligated in the form desired to generate the plasmids required. For analysis to confirm correct sequences in plasmids constructed, the ligation mixtures are used to transform host cells, and successful transformants selected by ampicillin or tetracycline resistance where appropriate. Plasmids from the transformants are prepared, analyzed by restriction endonuclease digestion, and/or sequenced.

Suitable host cells for cloning or expressing the DNA in the vectors herein are the prokaryote, yeast, or higher eukaryote cells described above. Suitable prokaryotes for this purpose include eubacteria, such as Gram-negative or Gram-positive organisms, for example, Enterobacteriaceae such as *Escherichia*, e.g., *E. coli, Enterobacter, Erwinia, Kebsiella, Proteus, Salmonella*, e.g., *Salmonella typhimurium, Serratia*, e.g., *Serratia marcescans*, and *Shigella*, as well as Bacilli such as *B. subtilis* and *B. licheniformis, Pseudomonas* such as *P. aeruginosa*, and *Streptomyces*. These examples are illustrative rather than limiting.

In addition to prokaryotes, eukaryotic microbes such as filamentous fungi or yeast are suitable expression hosts. *Saccharomyces cerevisiae*, or common baker's yeast, is the most commonly used among lower eukaryotic host microorganisms. However, a number of other genera, species, and strains are commonly available and useful herein, such as *Schizosaccharomyces pombe; Kluyveromyces* hosts such as *K. lactis, K. fragilis*, etc.; *Pichia pastoris; Candida; Neurospora crassa; Schwanniomyces* such as *Schwanniomyces occidentalis*; and filamentous fungi such as *Penicillium, Tolypocladium*, and *Aspergillus* hosts such as *A. nidulan*, and *A. niger*.

Examples of useful mammalian host cell lines are mouse L cells (L-M[TK-], ATCC #CRL-2648), monkey kidney CV1 line transformed by SV40 (COS-7, ATCC CRL 1651); human embryonic kidney line (293 or 293 cells subcloned for growth in suspension culture; baby hamster kidney cells (BHK, ATCC CCL 10); Chinese hamster ovary cells/-DHFR (CHO); mouse sertoli cells (TM4); monkey kidney cells (CV1 ATCC CCL 70); African green monkey kidney cells (VERO-76, ATCC CRL-1 587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells; MRC 5 cells; FS4 cells; and a human hepatoma line (Hep G2).

Host cells are transfected with the above-described expression vectors for Wnt signaling agonist or antagonist production, and cultured in conventional nutrient media modified as appropriate for inducing promoters, selecting transformants, or amplifying the genes encoding the desired sequences. Mammalian host cells may be cultured in a variety of media. Commercially available media such as Ham's F10 (Sigma), Minimal Essential Medium ((MEM), Sigma), RPMI 1640 (Sigma), and Dulbecco's Modified Eagle's Medium ((DMEM), Sigma) are suitable for culturing the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleosides (such as adenosine and thymidine), antibiotics, trace elements, and glucose or an equivalent energy source. Any other necessary supplements may also be included at appropriate concentrations that would be known to those skilled in the art. The culture conditions, such as temperature, pH and the like, are those previously used with the host cell selected for expression, and will be apparent to the ordinarily skilled artisan.

Methods of Use

In certain methods of the present invention, an effective amount of a composition comprising a Wnt agonist or antagonist is provided to cells, e.g. by contacting the cell with an effective amount of that composition to achieve a desired effect, e.g. to enhance Wnt signaling, proliferation, etc. In particular embodiments, the contacting occurs in vitro, ex vivo or in vivo. In particular embodiments, the cells are derived from or present within a subject in need or increased Wnt signaling.

In some methods of the invention, an effective amount of the subject composition is provided to enhance Wnt signaling in a cell. Biochemically speaking, an effective amount or effective dose of a Wnt agonist or antagonist is an amount to alter Wnt signaling in a cell by at least 30%, at least 40%, at least 50%, at least 60%, at least 70%, at least 80%, at least 90%, at least 95%, or by 100% relative to the signaling in the absence of the Wnt agonist or antagonist. The amount of modulation of a cell's activity can be determined by a number of ways known to one of ordinary skill in the art of Wnt biology.

In a clinical sense, an effective dose of a Wnt agonist or antagonist composition is the dose that, when administered to a subject for a suitable period of time, e.g., at least about one week, and may be about two weeks, or more, up to a period of about 4 weeks, 8 weeks, or longer, will evidence an alteration in the symptoms associated with lack of Wnt signaling. In some embodiments, an effective dose may not only slow or halt the progression of the disease condition but may also induce the reversal of the condition. It will be understood by those of skill in the art that an initial dose may be administered for such periods of time, followed by maintenance doses, which, in some cases, will be at a reduced dosage.

Cells in vitro may be contacted with a composition comprising a Wnt agonist or antagonist by any of a number of well-known methods in the art. For example, the composition may be provided to the cells in the media in which the subject cells are being cultured. Nucleic acids encoding the Wnt agonist or antagonist may be provided to the subject cells or to cells co-cultured with the subject cells on vectors under conditions that are well known in the art for promoting their uptake, for example electroporation, calcium chloride transfection, and lipofection. Alternatively, nucleic acids encoding the Wnt agonist or antagonist may be provided to the subject cells or to cells cocultured with the subject cells via a virus, i.e. the cells are contacted with viral particles comprising nucleic acids encoding the Wnt peptide agonist or antagonist polypeptide. Retroviruses, for example, lentiviruses, are particularly suitable to the method of the invention, as they can be used to transfect non-dividing cells (see, for example, Uchida et al. (1998) P.N.A.S. 95(20):11939-44). Commonly used retroviral vectors are "defective", i.e. unable to produce viral proteins required for productive infection. Rather, replication of the vector requires growth in a packaging cell line.

Likewise, cells in vivo may be contacted with the subject Wnt agonist or antagonist compositions by any of a number of well-known methods in the art for the administration of peptides, small molecules, or nucleic acids to a subject. The Wnt agonist or antagonist composition can be incorporated into a variety of formulations or pharmaceutical compositions, which in some embodiments will be formulated in the absence of detergents, liposomes, etc., as have been described for the formulation of full-length Wnt proteins.

Wnt signaling is a key component of stem cell culture. For example, the stem cell culture media as described in WO2010/090513, WO2012/014076, Sato et al., 2011 (GASTROENTEROLOGY 2011; 141:1762-1772) and Sato et al., 2009 (Nature 459, 262-5). The Wnt signaling agonists of the invention are suitable alternatives to Rspondin for use in these stem cell culture media, or may be combined with Rspondin.

Accordingly, in one embodiment, the invention provides a method for enhancing the proliferation of stem cells comprising supplying stem cells with agonists of the invention. In one embodiment, the invention provides a cell culture medium comprising one or more agonists of the invention. In some embodiments, the cell culture medium may be any cell culture medium already known in the art that normally comprises Wnt or Rspondin, but wherein the Wnt or Rspondin is replaced (wholly or partially) or supplemented by agonists of the invention. For example, the culture medium may be as described in as described in WO2010/090513, WO2012/014076, Sato et al., 2011 (GASTROENTEROLOGY 2011; 141:1762-1772) and Sato et al., 2009 (Nature 459, 262-5), which are hereby incorporated by reference in their entirety.

Stem cell culture media often comprise additional growth factors. This method may thus additionally comprise supplying the stem cells with a growth factor. Growth factors commonly used in cell culture medium include epidermal growth factor (EGF, (Peprotech), Transforming Growth Factor-alpha (TGF-alpha, Peprotech), basic Fibroblast Growth Factor (bFGF, Peprotech), brain-derived neurotrophic factor (BDNF, R&D Systems), Human Growth Factor (HGF) and Keratinocyte Growth Factor (KGF, Peprotech, also known as FGF7). EGF is a potent mitogenic factor for a variety of cultured ectodermal and mesodermal cells and has a profound effect on the differentiation of specific cells in vivo and in vitro and of some fibroblasts in cell culture. The EGF precursor exists as a membrane-bound molecule which is proteolytically cleaved to generate the 53-amino acid peptide hormone that stimulates cells. EGF or other mitogenic growth factors may thus be supplied to the stem cells. During culturing of stem cells, the mitogenic growth factor may be added to the culture medium every second day, while the culture medium is refreshed preferably every fourth day. In general, a mitogenic factor is selected from the groups consisting of: i) EGF, TGF-.alpha. and KGF, ii) EGF, TGF-.alpha. and FGF7; iii) EGF, TGF-.alpha. and FGF; iv) EGF and KGF; v) EGF and FGF7; vi) EGF and a FGF; vii) TGF-α and KGF; viii) TGF-.alpha. and FGF7; ix) or from TGF α and a FGF.

These methods of enhancing proliferation of stem cells can be used to grow new organoids and tissues from stem cells, as for example described in WO2010/090513 WO2012/014076, Sato et al., 2011 (GASTROENTEROLOGY 2011; 141:1762-1772) and Sato et al., 2009 (Nature 459, 262-5).

Compositions

For use in cell culture the Wnt signaling agonist or antagonist may be provided in culture medium, or may be provided in a form useful to diluting into culture medium. For therapeutic applications, the Wnt signaling agonist or antagonist may be administered to a mammal, preferably a human, in a physiologically acceptable dosage form, including those that may be administered to a human intravenously as a bolus or by continuous infusion over a period of time. Alternative routes of administration include topical, intramuscular, intraperitoneal, intra-cerobrospinal, subcutaneous, intra-articular, intrasynovial, intrathecal, oral, topical, or inhalation routes. The Wnt agonist or antagonists also are suitably administered by intratumoral, peritumoral, intralesional, or perilesional routes or to the lymph, to exert local as well as systemic therapeutic effects.

Pharmaceutical compositions may also comprise combinations of the molecules of the invention with cells, including stem cells, progenitor cells, and the like. In some embodiments, the compositions comprise the molecules of the invention in combination with regenerative somatic stem cells, e.g. epithelial stem cells, neural stem cells, liver stem cells, hematopoietic stem cells, osteoblasts, muscle stem cells, mesenchymal stem cells, pancreatic stem cells, etc. In such combinations, cells can be pre-treated with a molecule of the invention prior to use, e.g. ex vivo treatment of cells with the Wnt agonist or antagonist; cells can be administered concomitantly with a molecule of the invention in a separate or combined formulation; cells can be provided to an individual prior to treatment with a molecule of the invention, and the like.

Pharmaceutical compositions can include, depending on the formulation desired, pharmaceutically-acceptable, non-toxic carriers of diluents, which are defined as vehicles commonly used to formulate pharmaceutical compositions for animal or human administration. The diluent is selected so as not to affect the biological activity of the combination. Examples of such diluents are distilled water, buffered water, physiological saline, PBS, Ringer's solution, dextrose solution, and Hank's solution. In addition, the pharmaceutical composition or formulation can include other carriers, adjuvants, or non-toxic, nontherapeutic, nonimmunogenic stabilizers, excipients and the like. The compositions can also include additional substances to approximate physiological conditions, such as pH adjusting and buffering agents, toxicity adjusting agents, wetting agents and detergents. Further guidance regarding formulations that are suitable for various types of administration can be found in Remington's Pharmaceutical Sciences, Mace Publishing Company, Philadelphia, Pa., 17th ed. (1985). For a brief review of methods for drug delivery, see, Langer, Science 249:1527-1533 (1990).

The components used to formulate the pharmaceutical compositions are preferably of high purity and are substantially free of potentially harmful contaminants (e.g., at least National Food (NF) grade, generally at least analytical grade, and more typically at least pharmaceutical grade). Moreover, compositions intended for in vivo use are usually sterile. To the extent that a given compound must be synthesized prior to use, the resulting product is typically substantially free of any potentially toxic agents, particularly any endotoxins, which may be present during the synthesis or purification process. Compositions for parental administration are also sterile, substantially isotonic and made under GMP conditions.

In another embodiment of the invention, an article of manufacture containing materials useful for the treatment of the conditions described herein is provided. The article of manufacture comprises a container and a label. Suitable containers include, for example, bottles, vials, syringes, and test tubes. The containers may be formed from a variety of materials such as glass or plastic. The container holds a composition that is effective for treating the condition and may have a sterile access port (for example the container may be an intravenous solution bag or a vial having a stopper pierceable by a hypodermic injection needle). The active agent in the composition is the Wnt agonist or antagonist. The label on, or associated with, the container indicates that the composition is used for treating the condition of choice. Further container(s) may be provided with the article of manufacture which may hold, for example, a pharmaceutically-acceptable buffer, such as phosphate-buffered saline, Ringer's solution or dextrose solution. The article of manufacture may further include other materials desirable from a commercial and user standpoint, including other buffers, diluents, filters, needles, syringes, and package inserts with instructions for use.

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1

DFBss are genetically engineered antibody mimetic proteins typically exhibiting highly specific and high-affinity target protein binding. They are derived from natural ankyrin proteins, one of the most common classes of binding proteins in nature, which are responsible for diverse functions such as cell signaling, regulation and structural integrity of the cell. DFBs consist of at least three, repeat motifs proteins, and usually consist of four or five, of which the first (N-capping repeat) and last (C-capping repeat) serve to provide a hydrophilic surface. Their molecular mass is about 14 or 18 kDa for four- or five-repeat DFBs, respectively.

DFBs are derived from naturally occurring ankyrin proteins, a protein class that mediates high-affinity protein-protein interactions in nature. DFBs can be expressed in the cytoplasm of *Escherichia coli* at high levels in soluble form. The proteins exhibit high thermal and thermodynamic stability increasing with increasing repeat number.

A protein scaffold was based on the Rosetta-built idealized Ankyrin repeat protein (PDB: 4GPM, see Fallas et al. (2017) Nat. Chem. 9:353-360). Starting from this scaffold, we combined computational design and in vitro evolution with yeast surface display to evolve high affinity Wnt antagonists. Rosetta was used to build the idealized Ankyrin repeat protein and we further allowed randomization at positions permitted by Rosetta calculation to retain original packing.

SEQ ID NO:1-4 provide the amino acid sequences of the antagonist proteins thus developed, which have the following sequences and frizzled specificity:

1AF34 comprises the amino acid sequence set forth in SEQ ID NO:1. It binds with high affinity to human frizzled proteins Fzd1, Fzd2, Fzd5, Fzd7, Fzd8. The sequence of the mature protein is as follows, although it may be noted that the last two residues (LE) provide a flexible loop but may be deleted without affecting activity.

SEQ ID NO: 1
SELGTRLIRAALDGNKDRVKDLIENGADVNASLMSGATPLHAAAMNGHKE

VVKLLISKGADVNAQSVAGSTPLDAAAFSGHKEVVKLLISKGADVNAVNA

AGLTPLHAAADNGHKEVVKLLISKGADVNAKADHGMTPLHFAAQRGHKEV

VKLLISKGADLNTSAKDGATPLDMARESGNEEVVKLLEKQLE

ANK12 comprises the amino acid sequence set forth in SEQ ID NO:2. It binds with high affinity to human frizzled proteins Fzd5, Fzd8. The sequence of the mature protein is as follows:

SEQ ID NO: 2
SELGKRLIMAALDGNKDRVKDLIENGADVNASLVSGATPLHAAAMNGHKE

VVKLLISKGADVNAQSAAGSTPLAAAAINGHKEVVKLLISKGADVNAVTA

AGMTPLHAAAANGHKEVVKLLISKGADVNAKADRGMTPLHFAAWRGHKEV

VKLLISKGADLNTSAKDGATPLDMARESGNEEVVKLLEKQLE

1AF34F7 comprises the amino acid sequence set forth in SEQ ID NO:3. It binds with high affinity to human frizzled proteins Fzd1, Fzd2, Fzd7. The sequence of the mature protein is as follows:

SEQ ID NO: 3
SELGTRLIRAALDGNKDRVKDLIENGADVNASLMSGATPLHAAAMNGHKE

VVKLLISKGADVNAQSVAGSTPLDAAAFSGHKEVVKLLISKGADVNAVNA

AGLTPLHDAADDGHNEVVKLLISKGADVNAKADHGMTPLHFAAQRGHKEV

VKLLISKGADLNTSAKDGATPLDMARESGNEEVVKLLEKQLE

4AF30 comprises the amino acid sequence set forth in SEQ ID NO:4. It binds with high affinity to human frizzled protein Fzd4. The sequence of the mature protein is as follows:

SEQ ID NO: 4
SELGKRLIRAALDGNKDRVKDLIENGADVNASLMSGTTPLYAAAMNGHKE

VVKLLISKGADVNAQSVAGSTPLVAAANFGHNEVVKLLISKGADVNAVTA

FGVTPLHAAAADGHKEVVKLLISKGADVNAKAGRGMTPLHIAAFRGHKEV

VKLLISKGADLNTSAKDGATPLDMARESGNEEVVKLLEKQLE

To understand the affinity of individual DFBs towards different Fzd CRDs, two different methods were used to measure the specificity and affinity. DFBs were expressed on yeast surface and the yeast stained with biotinylated Fzd CRDs. The cells were washed and Streptavidin, Alexa Fluor™ 647 conjugates were used to stain the yeasts. The fluorescence signals were read on flow cytometry.

Second, individual DFB proteins were purified and surface Plasmon Resonance (SPR) used to measure the affinity between Fzd CRD with the DFB. The biotinylated Fzd CRD was captured on SA sensor chip at low density. A gradient concentration of DFB analyte was flown over the chip. The data was analyzed by BIACore accompanying software.

Figure 1B:
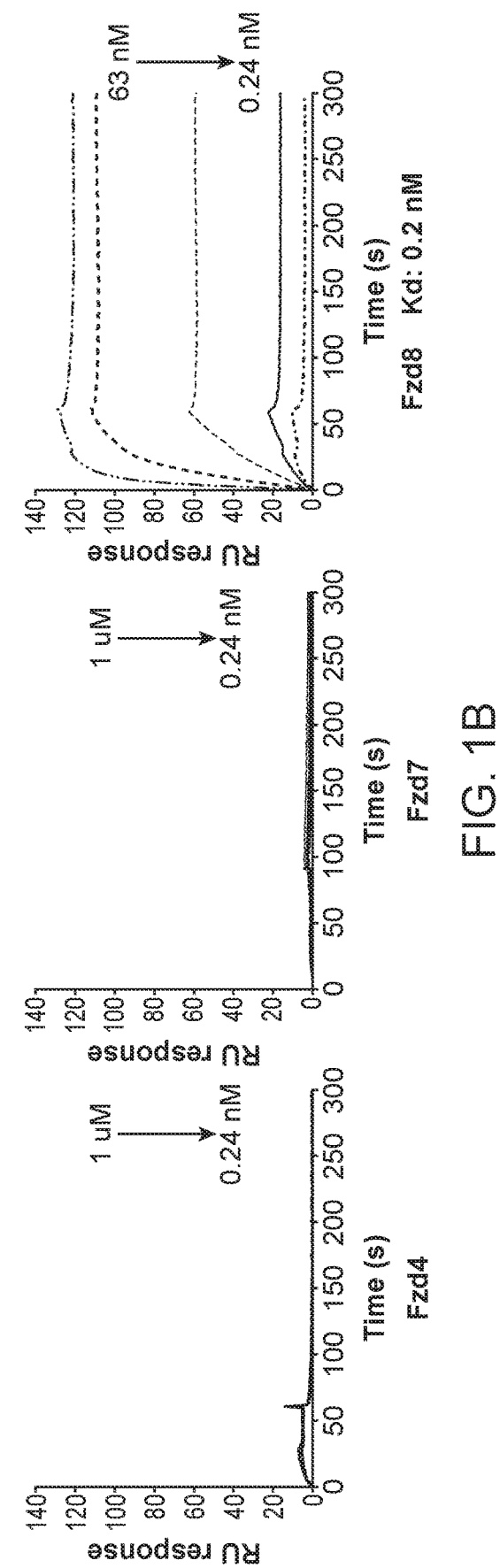

The results of these experiments are shown in FIGS. 1A and 1B. FIG. 1A shows the results of ANK12 yeast titration with individual Fzd CRD. ANK12 showed $EC_{50}$ of 4.4 nM and 3.6 nM for Fz5 and Fz8 while not interacting with Fz1, 2, 4 and 7. FIG. 1B shows the SPR results of ANK12 to Fzd4, 7 and 8. ANK12 showed no binding to Fzd4 or Fzd7 while showing a Kd of 200 pM for Fzd8. Collectively, ANK12 showed high specificity and affinity to Fzd5 and Fzd8.

Figure 2:
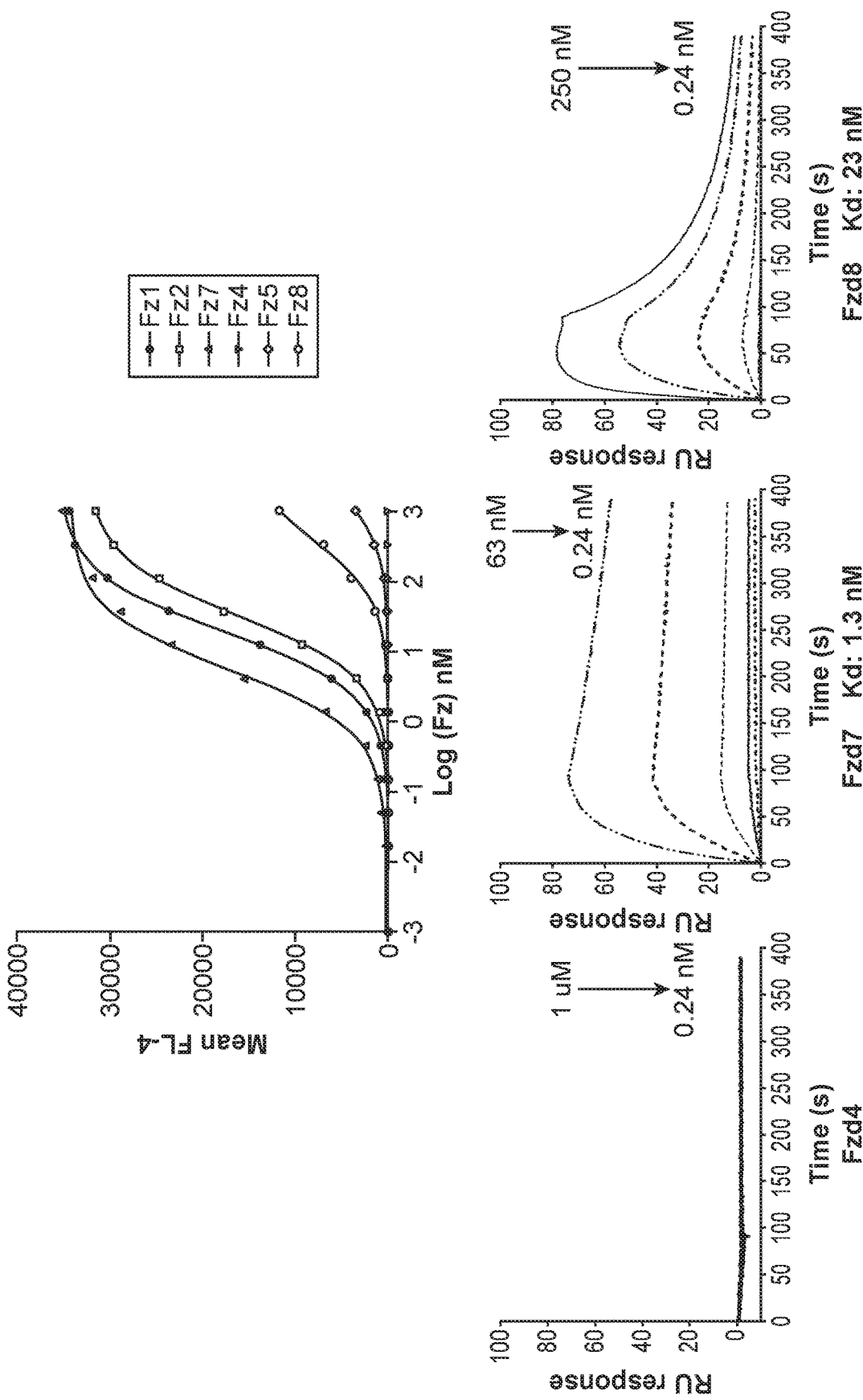
FIG. 2. Affinity measurement of 1AF34, 1AF34F7 and 4AF30 towards different Fzds.
Figure 3:
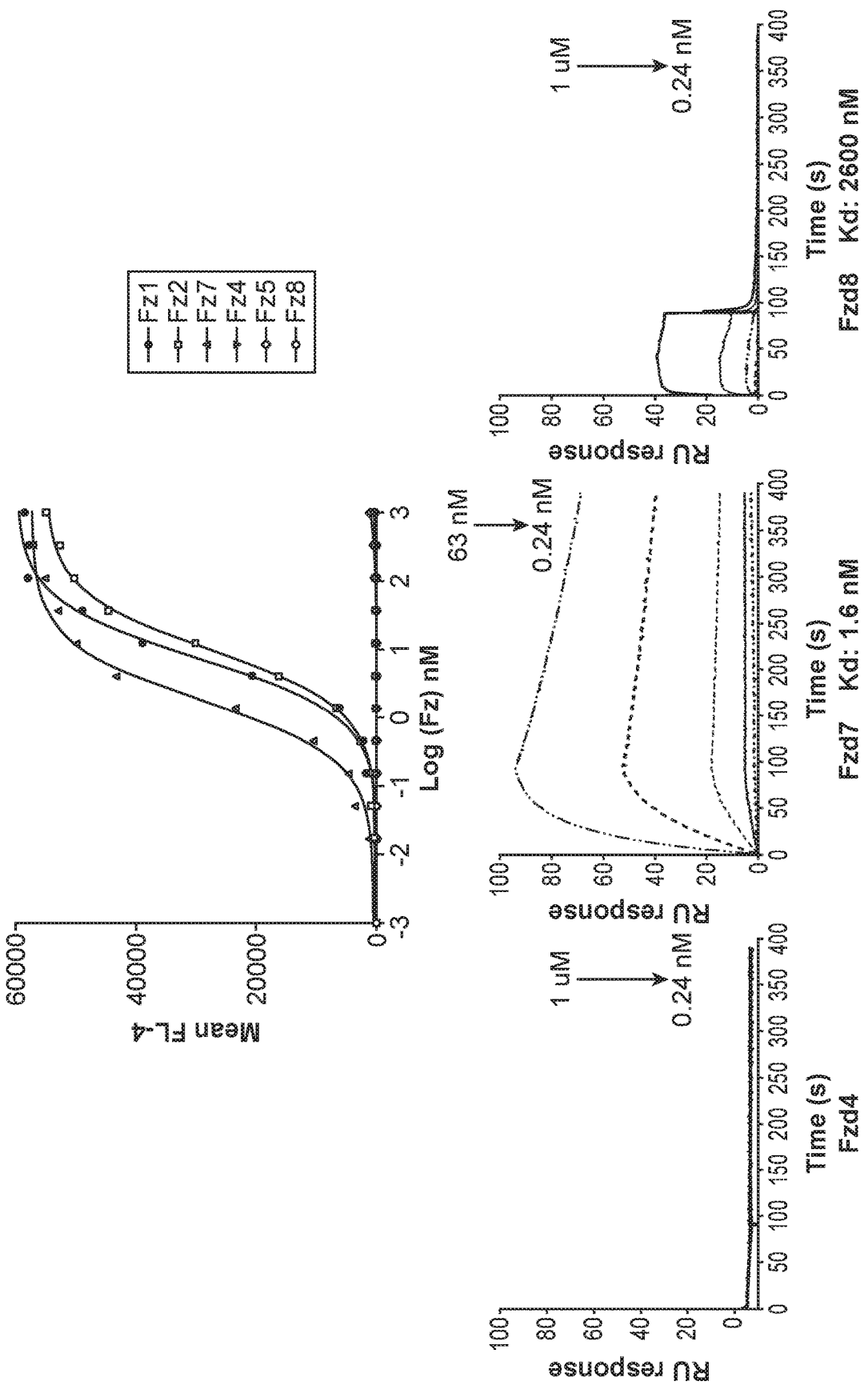
FIG. 3. Affinity measurement of 1AF34F7.
Figure 4:
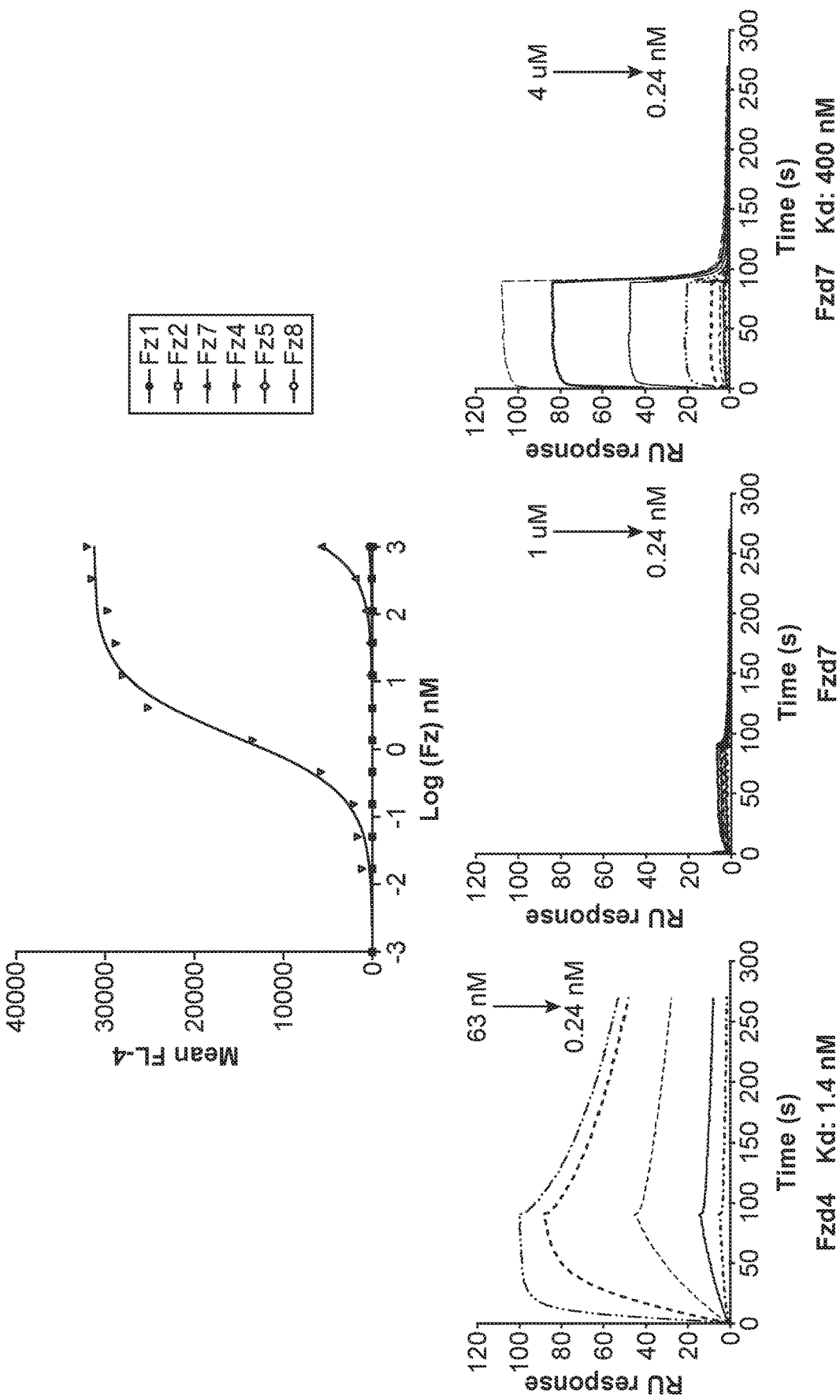
FIG. 4. Affinity measurement of 4AF30.

Similar affinity measurement of 1AF34, 1AF34F7 and 4AF30 towards different Fzds using both methods were performed, as shown in FIG. 2. 1AF34 showed $EC_{50}$ of 19.0, 31.6 and 5.6 nM to Fz1, 2 and 7. 1AF34 showed weaker staining to Fz5/8 with $EC_{50}$ not available. By SPR, 1AF34 binds to Fzd7 at 1 nM affinity and Fzd8 at 23 nM affinity. Shown in FIG. 3, 1AF34F7 showed $EC_0$ of 7.5 nM, 9.9 nM and 1.8 nM to Fz1, 2 and 7, respectively. 1AF34F7 showed no cross-reactivity to Fz5/8 up to 1 µM concentration. Using SPR, 1AF34F7 shows 1.6 nM affinity to Fzd7 CRD. Shown in FIG. 4, 4AF30 only binds to Fz4 with $EC_{50}$ of 1.6 nM. Using SPR, 4AF30 shows 1.4 nM affinity to Fzd4 and 400 nM for Fzd8.

To generate Fzd subtype specific Wnt agonists, the DFBs were fused with DKK1c to generate bi-specific molecules that bridge specific Fzd receptors with co-receptors Lrp5/6 to activate canonical Wnt signaling. The amino acid sequence of all four DFBs agonists are set forth in SEQ ID NO:5-8.

SEQ ID NO:5-8 provide the amino acid sequences of the agonist proteins thus developed, which have the following sequences and frizzled specificity:

1AF34-DKK1c comprises the amino acid sequence set forth in SEQ ID NO:5. It binds with high affinity to human frizzled proteins Fzd1, Fzd2, Fzd5, Fzd7, Fzd8. The sequence of the mature protein is as follows. Amino acid residues 1-192 correspond to SEQ ID NO:1, residues 193-202 are a 10 mer GS linker, residues 203-292 correspond to human DKK1c.

SEQ ID NO: 5
SELGTRLIRAALDGNKDRVKDLIENGADVNASLMSGATPLHAAAMNGHKE

VVKLLISKGADVNAQSVAGSTPLDAAAFSGHKEVVKLLISKGADVNAVNA

AGLTPLHAAADNGHKEVVKLLISKGADVNAKADHGMTPLHFAAQRGHKEV

VKLLISKGADLNTSAKDGATPLDMARESGNEEVVKLLEKQLEGSGSGGSG

SGKIMYHTKGQEGSVCLRSSDCASGLCCARHFWSKICKPVLKEGQVCTKH

RRKGSHGLEIFQRCYCGEGLSCRIQKDHHQASNSSRLHTCQRH

ANK12-DKK1c comprises the amino acid sequence set forth in SEQ ID NO:6. It binds with high affinity to human frizzled proteins Fzd5, Fzd8. The sequence of the mature protein is as follows. Amino acid residues 1-192 correspond to SEQ ID NO:2, residues 193-202 are a 10 mer GS linker, residues 203-292 correspond to human DKK1c.

SEQ ID NO: 6
SELGKRLIMAALDGNKDRVKDLIENGADVNASLVSGATPLHAAAMNGHKE

VVKLLISKGADVNAQSAAGSTPLAAAAINGHKEVVKLLISKGADVNAVTA

AGMTPLHAAAANGHKEVVKLLISKGADVNAKADRGMTPLHFAAWRGHKEV

VKLLISKGADLNTSAKDGATPLDMARESGNEEVVKLLEKQLEGSGSGGSG

SGKMYHTKGQEGSVCLRSSDCASGLCCARHFWSKICKPVLKEGQVCTKHR

RKGSHGLEIFQRCYCGEGLSCRIQKDHHQASNSSRLHTCQRH

1AF34F7-DKK1c comprises the amino acid sequence set forth in SEQ ID NO:7. It binds with high affinity to human frizzled proteins Fzd1, Fzd2, Fzd7. The sequence of the mature protein is as follows. Amino acid residues 1-192 correspond to SEQ ID NO:3, residues 193-202 are a 10 mer GS linker, residues 203-292 correspond to human DKK1c.

SEQ ID NO: 7
SELGTRLIRAALDGNKDRVKDLIENGADVNASLMSGATPLHAAANANGHK

EVVKLLISKGADVNAQSVAGSTPLDAAAFSGHKEVVKLLISKGADVNAVN

AAGLTPLHDAADDGEINEVVKLLISKGADVNAKADHGMTPLHFAAQRGHK

EVVKLLISKGADLNTSAKDGATPLDMARESGNEEVVKLLEKQLEGSGSGG

SGSGKMYHTKGQEGSVCLRSSDCASGLCCARHFWSKICKPVLKEGQVCTK

HRRKGSHGLEIFQRCYCGEGLSCRIQKDHHQASNSSRLHTCQRH

4AF30-DKK1c comprises the amino acid sequence set forth in SEQ ID NO:8. It binds with high affinity to human frizzled protein Fzd4. The sequence of the mature protein is as follows. Amino acid residues 1-90 correspond to human DKK1c, residues 91-100 are a 10 mer GS linker, residues 101-292 correspond to SEQ ID NO:4.

SEQ ID NO: 8
KMYHTKGQEGSVCLRSSDCASGLCCARHFWSKICKPVLKEGQVCTKHRRK

GSHGLEIFQRCYCGEGLSCRIQKDHHQASNSSRLHTCQRHGSGSGGSGSG

SELGKRLIRAALDGNKDRVKDLIENGADVNASLMSGTTPLYAAAMNGHKE

VVKLLISKGADVNAQSVAGSTPLVAAANFGHNEVVKLLISKGADVNAVTA

FGVTPLHAAAADGHKEVVKLLISKGADVNAKAGRGMTPLHIAAFRGHKEV

VKLLISKGADLNTSAKDGATPLDMARESGNEEVVKLLEKQLE

Figure 5A:
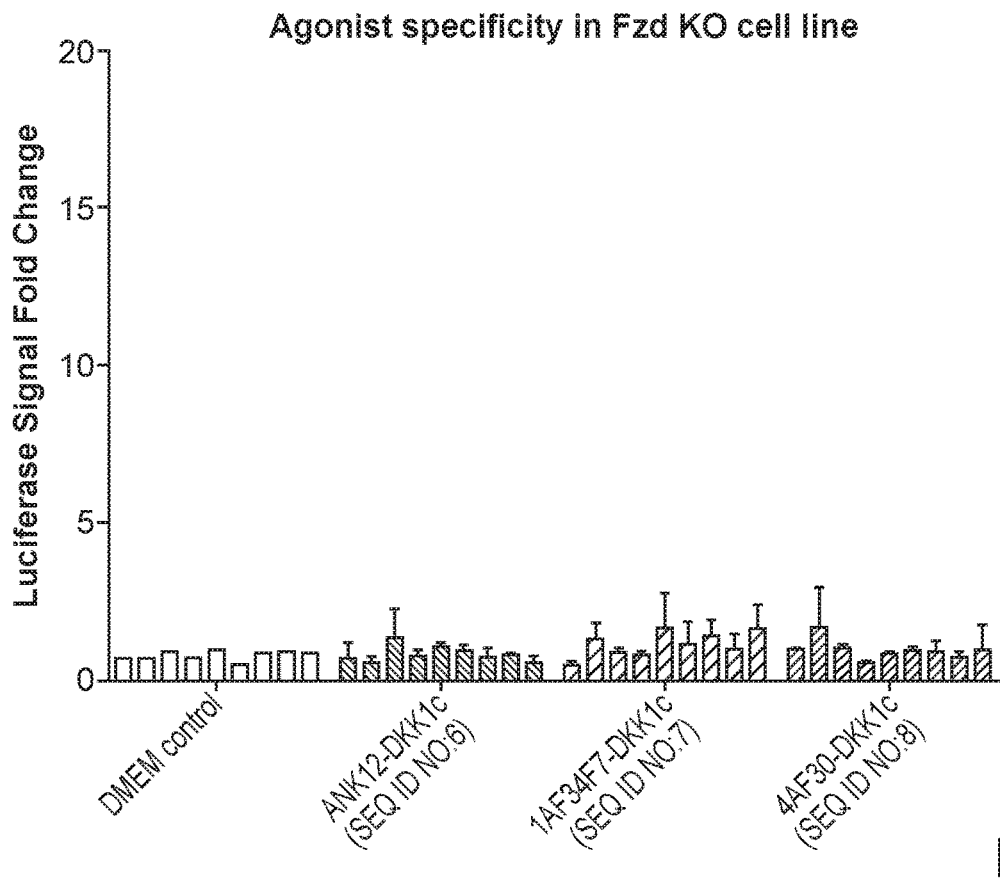
FIG. 5A-5D.
Figure 5B:
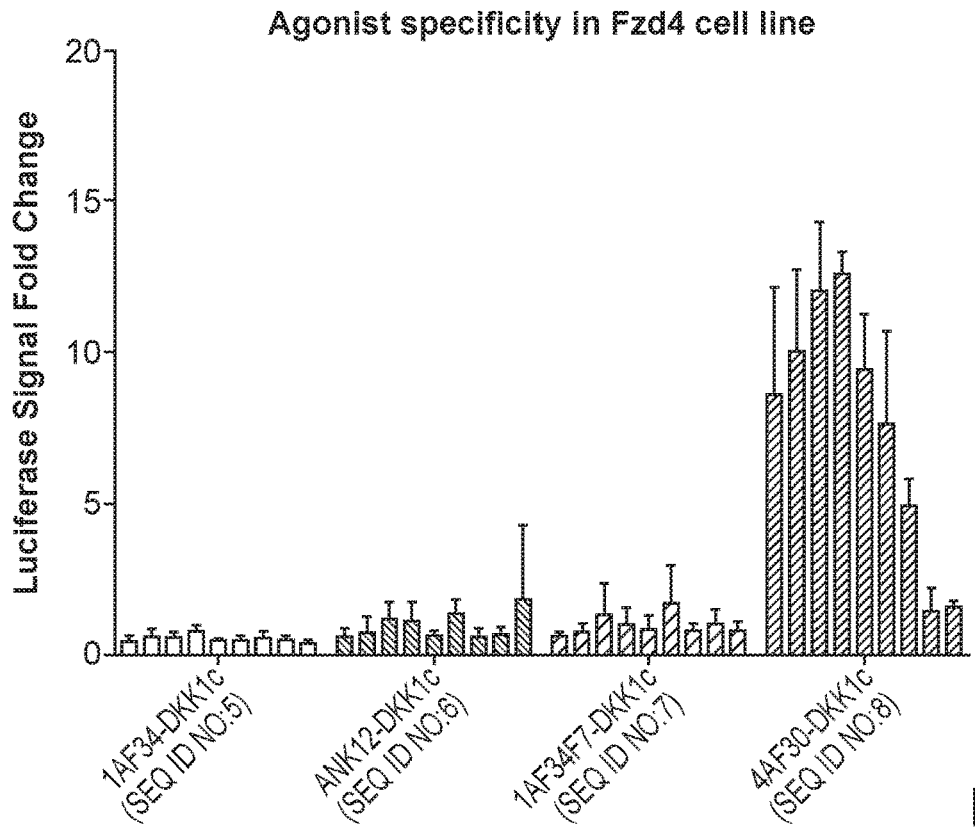

To confirm the Fz specificity of each DFBs agonist of SEQ ID NO:5-8, the HEK293T cell line with Fzd1/2/4/5/7/8 knockout was used. Shown in FIG. 5A, the Wnt agonists show no activity in this knockout cell line. Mouse Fzd4 receptor was transfected into the cell line and stimulated with all four types of Wnt agonists. Only Fzd4 specific agonist (4AF30-DKK1c, shown in FIG. 5B) showed potent activation of Wnt signaling, shown by SuperTop Flash Wnt reporter assays.

Figure 5C:
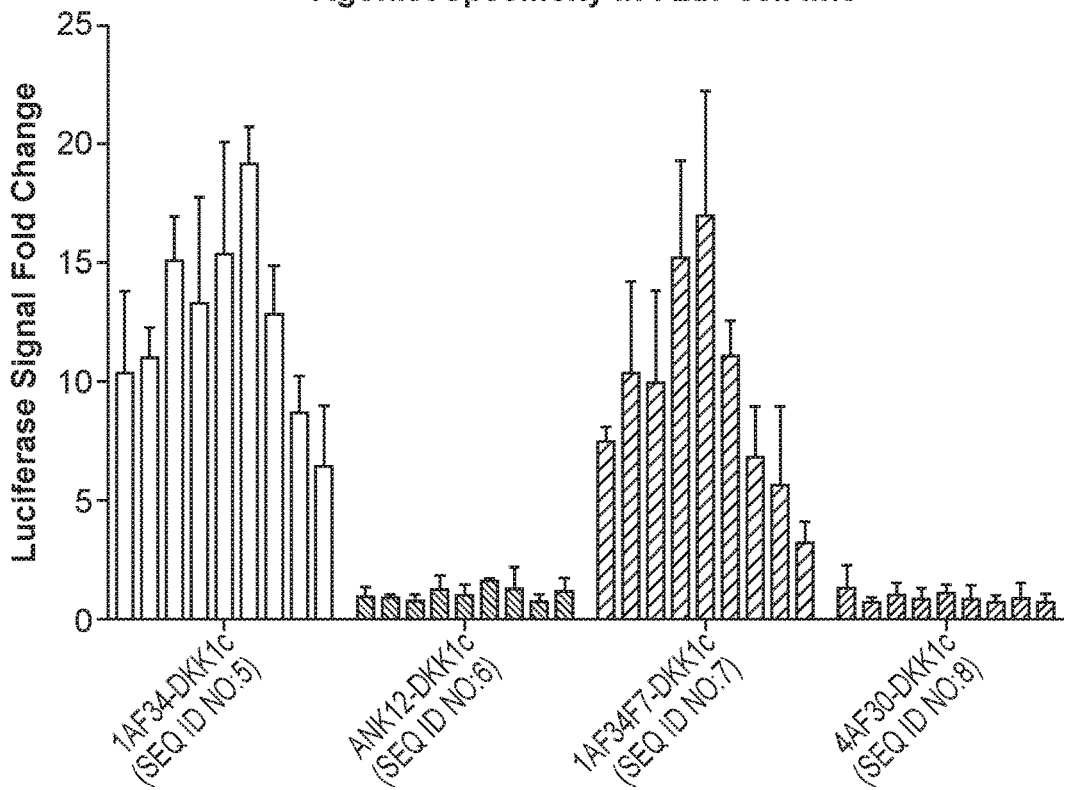
Figure 5D:
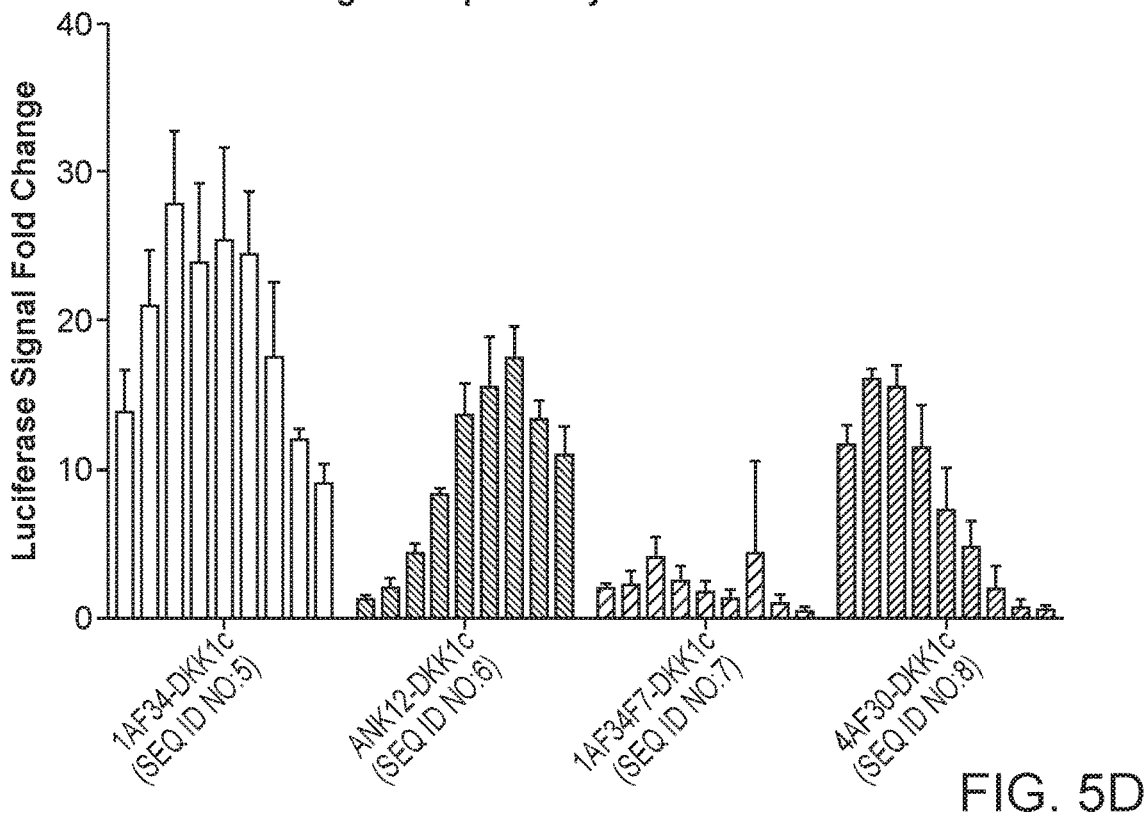

Shown in FIGS. 5C and D, mouse Fzd7 and Fzd8 receptor was transfected into the cell line and stimulated with all four types of agonist or antagonist agonists. In the cells with transfected Fz7 receptor, two of the agonists (1AF34-DKK1c and 1AF34F7-DKK1c) showed potent activation of Wnt signaling, shown by SuperTop Flash assays. In the cells transfected with Fz8 receptors, two of the agonists (1AF34-DKK1c and ANK12-DKK1c) showed potent activation of Wnt signaling. Fzd4 specific agonist (4AF30-DKK1c) showed activation of Wnt signaling, but the activity is diminished significantly at low concentration (<3 nM). The Fzd agonist specificity is consistent with their specificity to Fzd CRD, as shown by SPR.

Figure 6:
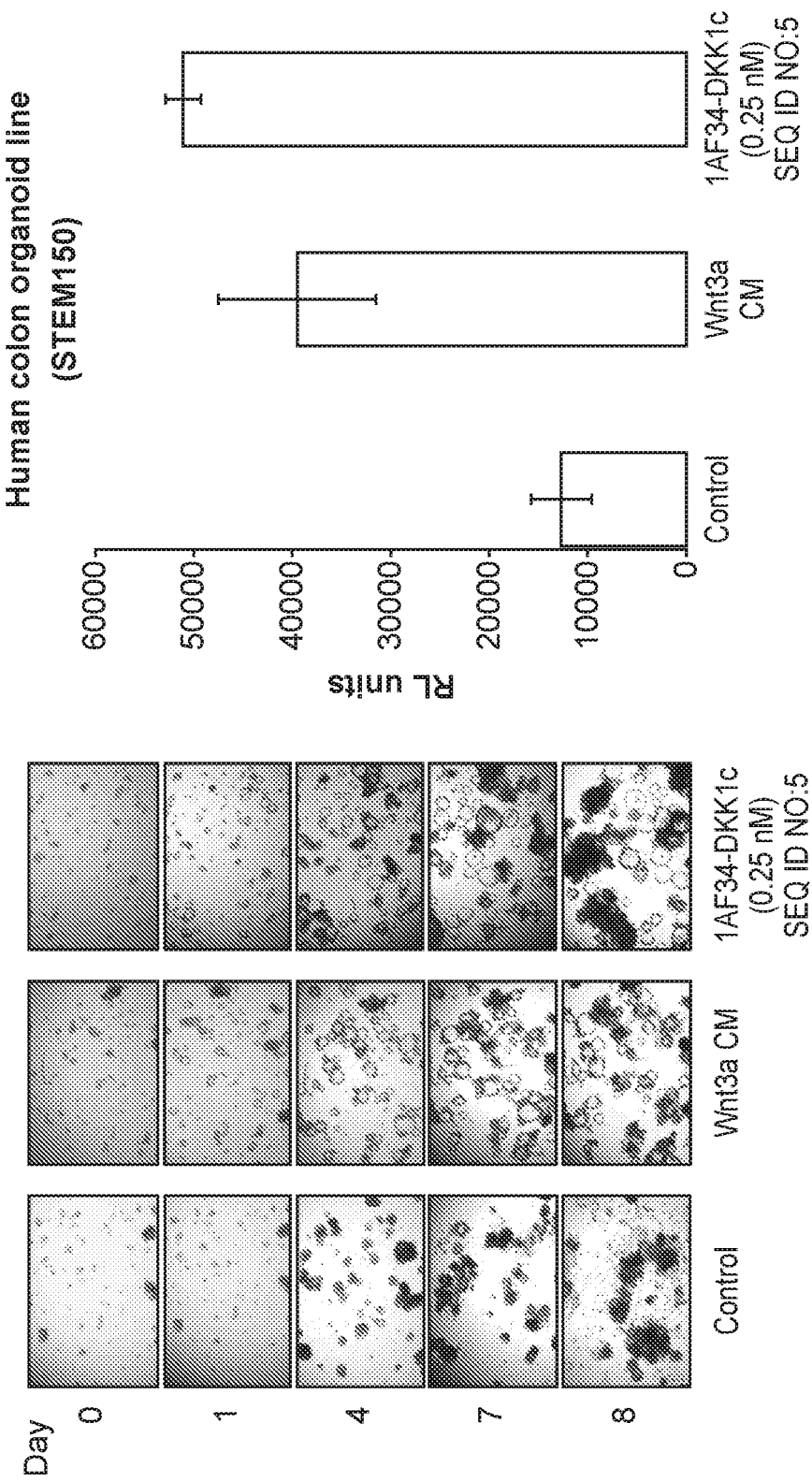
FIG. 6. Activity of Wnt agonist in supporting human colon organoid growth.
Figure 7:
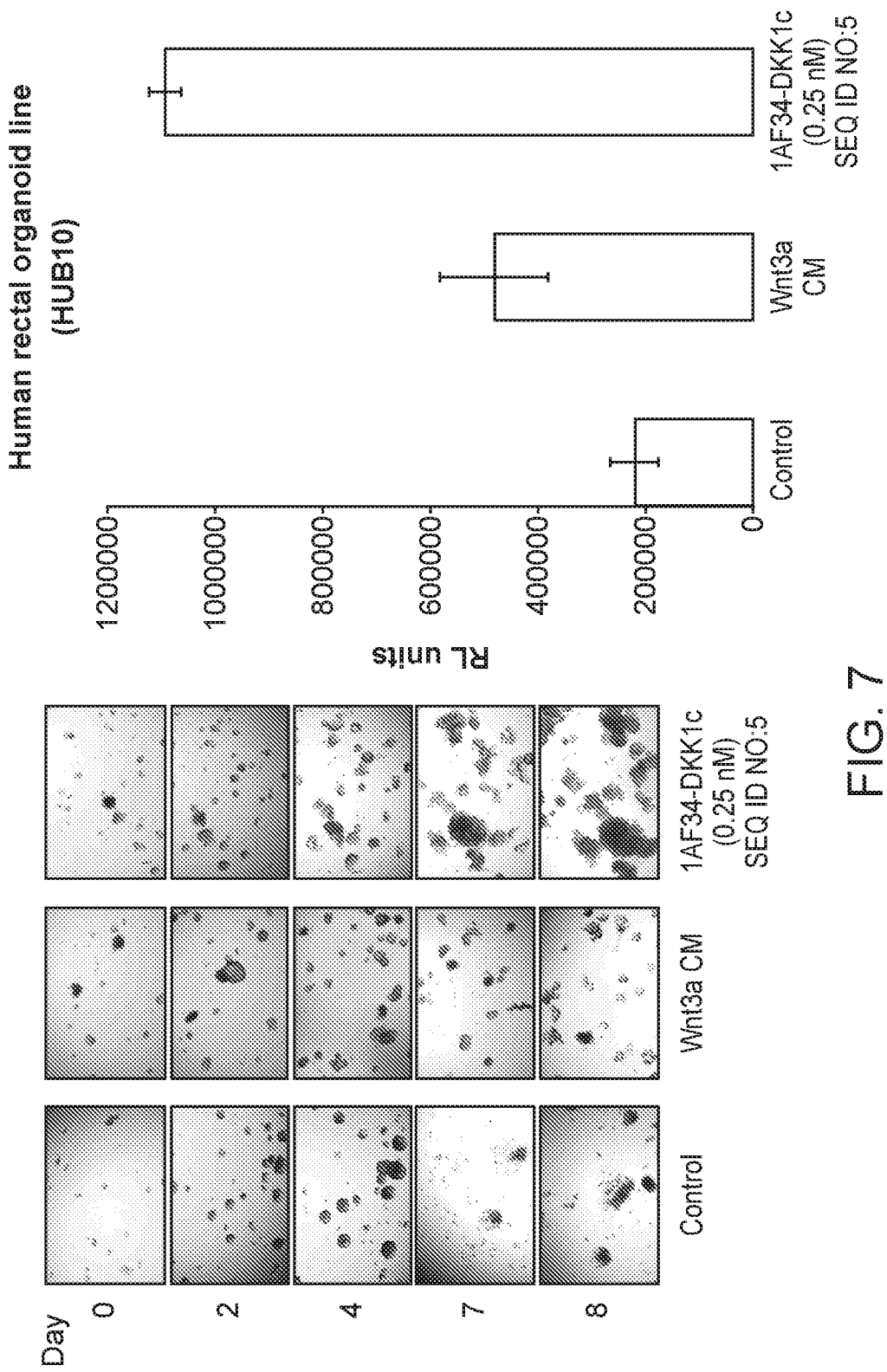
FIG. 7. Activity of Wnt agonist in supporting human rectal organoid.

Having confirmed the specificity of our DFBs based Wnt agonists, it was determined if the agonist was active in supporting organoid growth. The Wnt agonist 1AF34-DKK1c (SEQ ID NO:5), which has broad spectrum of activity for most Fz receptors (Fz1/2/5/7/8) was tested, shown in FIG. 6. Wnt3a conditioned media (CM) was used as control to our Wnt agonist (1AF34-DKK1c at 0.25 nM) in supporting human colon organoid growth. The agonist or antagonist Wnt agonist not only support human colon organoid growth but also shows better growth compared to Wnt3a CM. Shown in FIG. 7 are similar experiments on human rectal organoid. The agonist or antagonist Wnt agonist also supports rectal organoid and shows better response compared to Wnt3a CM.

The coding sequence for SEQ ID NO:5 was designed, in one iteration, as SEQ ID NO:9:

GGATCCTCTGAACTGGGTACGCGTCTGATCAGGGCAGCATTAGACGGTAA

CAAAGACCGTGTTAAAGACCTCATTGAAAATGGTGCTGACGTTAACGCGT

CCCTTATGTCTGGGGCGACTCCGTTACACGCCGCCGCCATGAACGGCCAC

AAAGAGGTTGTGAAGTTACTGATCTCCAAGGGCGCAGATGTGAATGCTCA

GTCCGTTGCGGGTTCTACACCTCTGGATGCGGCGGCGTTTAGTGGACATA

AAGAAGTGGTAAAACTGCTGATAAGTAAAGGAGCAGACGTCAATGCTGTT

AATGCGGCTGGATTGACCCCCCTACATGCTGCTGCTGATAATGGGCACAA

GGAAGTAGTGAAGTTGCTTATTTCTAAGGGGGCCGACGTAAATGCGAAAG

CTGACCATGGCATGACTCCACTCCATTTCGCAGCACAGCGCGGTCATAAG

GAAGTCGTTAAACTATTAATCAGCAAAGGTGCGGATTTGAACACCTCTGC

CAAAGACGGTGCAACCCCGCTTGACATGGCGCGTGAATCTGGCAATGAGG

AGGTTGTCAAGCTCTTGGAAAAGCAACTCGAGGGAAGCGGTTCCGGAGGT

TCTGGCTCCGGAAAAATGTATCACACTAAGGGACAGGAAGGCAGCGTGTG

CCTGAGGTCCTCTGACTGTGCATCTGGCCTGTGCTGCGCCAGACACTTTT

GGTCCAAAATCTGCAAGCCGGTTCTGAAAGAGGGCCAGGTGTGCACAAAG

CATCGACGAAAGGGCAGCCATGGACTCGAGATCTTTCAGAGGTGCTACTG

CGGGGAGGGTCTGTCTTGCAGAATCCAGAAAGATCATCATCAGGCCTCCA

ACTCCTCCCGCCTGCACACCTGCCAGCGACATGCGGCCGC

In another version, the coding sequence for SEQ ID NO:5 was optimized for expression in human cells, e.g. in HEK cells, show as SEQ ID NO:10:

GGATCCAGCGAACTCGGCACCCGACTTATCAGAGCTGCCCTTGATGGAAA

TAAGGACCGGGTCAAAGACCTGATAGAGAATGGGGCGGACGTTAATGCAA

GTCTTATGTCCGGTGCTACCCCGTTGCATGCCGCTGCAATGAATGGCCAC

AAGGAGGTTGTAAAATTGCTCATAAGTAAAGGCGCAGACGTAAACGCACA

ATCCGTGGCGGGCAGTACCCCCTTGGATGCCGCTGCGTTCTCAGGCCATA

AAGAGGTCGTAAAACTGCTGATCTCCAAAGGAGCGGACGTCAATGCAGTA

AATGCTGCAGGACTTACCCCCTTGCACGCCGCTGCCGACAATGGACACAA

GGAGGTTGTAAAACTTCTCATATCTAAAGGCGCGGACGTCAACGCTAAAG

CGGACCACGGAATGACGCCGCTCCACTTTGCGGCACAGAGGGGCCATAAA

GAGGTAGTGAAACTTCTGATCTCAAAAGGAGCCGACTTGAATACGAGCGC

TAAGGATGGTGCAACGCCATTGGATATGGCCAGGGAGTCCGGAAATGAAG

AGGTGGTGAAGCTGCTTGAGAAGCAACTCGAAGGTAGCGGGAGCGGCGGG

AGTGGCTCTGGCAAGATGTACCATACCAAGGGCCAAGAAGGGAGTGTGTG

CCTGCGGTCAAGCGACTGCGCATCAGGCTTGTGCTGTGCTAGGCATTTCT

GGTCCAAGATTTGTAAGCCAGTATTGAAGGAAGGCCAGGTGTGTACTAAA

CATAGGCGCAAGGGAAGTCATGGTCTCGAGATATTCCAACGCTGTTACTG

TGGCGAGGGATTGTGTTGCCGCATACAAAAAGACCACCACCAGGCGTCTA

ACTCTAGTAGGCTTCACACATGCCAACGGCACGCGGCCGC

For some purposes, for example protein stability and expression, the Wnt agonist proteins described herein are joined to an Fc sequences, including for example human IgG1, shown in SEQ ID NO:11

GCTAGCACCAAGGGCCCATCGGTCTTCCCCCTGGCACCCTCCTCCAAGAG

CACCTCTGGGGGCACAGCGGCCCTGGGCTGCCTGGTCAAGGACTACTTCC

CCGAACCGGTGACGGTGTCGTGGAACTCAGGCGCCCTGACCAGCGGCGTG

CACACCTTCCCGGCTGTCCTACAGTCCTCAGGACTCTACTCCCTCAGCAG

CGTGGTGACCGTGCCCTCCAGCAGCTTGGGCACCCAGACCTACATCTGCA

ACGTGAATCACAAGCCCAGCAACACCAAGGTGGACAAGAAAGTTGAGCCC

AAATCTTGTGACAAAACTCACACATGCCCACCGTGCCCAGCACCTGAACT

CCTGGGGGACCGTCAGTGTTCCTCTTCCCCCCAAAACCCAAGGACACCC

TCATGATCTCCCGGACCCCTGAGGTCACATGCGTGGTGGTGGACGTGAGC

CACGAAGACCCTGAGGTCAAGTTCAACTGGTACGTGGACGGCGTGGAGGT

GCATAATGCCAAGACAAAGCCGCGGGAGGAGCAGTACAACAGCACGTACC

GTGTGGTCAGCGTCCTCACCGTCCTGCACCAGGACTGGCTGAATGGCAAG

GAGTACAAGTGCAAGGTCTCCAACAAAGCCCTCCCAGCCCCCATCGAGAA

AACCATCTCCAAAGCCAAAGGGCAGCCCCGAGAACCACAGGTGTACACCC

TGCCCCCATCCCGGAGGAGATGACCAAGAACCAGGTCAGCCTGACCTGC

CTGGTCAAAGGCTTCTATCCCAGCGACATCGCCGTGGAGTGGGAGAGCAA

TGGGCAGCCGGAGAACAACTACAAGACCACGCCTCCCGTGCTGGACTCCG

ACGGCTCCTTCTTCCTCTACAGCAAGCTCACCGTGGACAAGAGCAGGTGG

CAGCAGGGGAACGTCTTCTCATGCTCCGTGATGCATGAGGCTCTGCACAA

CCACTACACGCAGAAGAGCCTCTCCCTGTCTCCGGGTAAATGA

The coding sequence of the construct for expression may have the sequence of SEQ ID NO:15:

ATGGCCCGGCCTCTGTGTACCCTGCTACTCCTGATGGCTACCCTGGCTGG

GGCTCTGGCCGGATCCAGCGAACTCGGCACCCGACTTATCAGAGCTGCCC

TTGATGGAAATAAGGACCGGGTCAAAGACCTGATAGAGAATGGGCGGAC

GTTAATGCAAGTGTTATGTCCGGTGCTACCCCGTTGCATGCCGCTGCAAT

GAATGGCCACAAGGAGGTTGTAAAATTGCTCATAAGTAAAGGCGCAGACG

TAAACGCACAATCCGTGGCGGGCAGTACCCCCTTGGATGCCGCTGCGTTC

TCAGGCCATAAAGAGGTCGTAAAACTGCTGATCTCCAAAGGAGCGGACGT

CAATGCAGTAAATGCTGCAGGACTTACCCCCTTGCACGCCGCTGCCGACA

ATGGACACAAGGAGGTTGTAAAACTTCTCATATCTAAAGGCGCGGACGTC

AACGCTAAAGCGGACCACGGAATGACGCCGCTCCACTTTGCGGCACAGAG

GGGCCATAAAGAGGTAGTGAAACTTCTGATCTCAAAAGGAGCCGACTTGA

ATACGAGCGCTAAGGATGGTGCAACGCCATTGGATATGGCCAGGGAGTCC

GGAAATGAAGAGGTGGTGAAGCTGCTTGAGAAGCAACTCGAAGGTAGCGG

GAGCGGCGGGAGTGGCTCTGGCAAGATGTACCATACCAAGGGCCAAGAAG

GGAGTGTGTGCCTGCGGTCAAGCGACTGCGCATCAGGCTTGTGCTGTGCT

AGGCATTTCTGGTCCAAGATTTGTAAGCCAGTATTGAAGGAAGGCCAGGT

GTGTACTAAACATAGGCGCAAGGGAAGTCATGGTCTCGAGATATTCCAAC

GCTGTTACTGTGGCGAGGGATTGTGTTGCCGCATACAAAAAGACCACCAC

CAGGCGTCTAACTCTAGTAGGCTTCACACATGCCAACGGCACGCGGCCGC

AGAGAACCTGTACTTCCAGGGATCTTCCGAGCCCAAATCTTGTGACAAAA

CTCACACATGCCCACCGTGCCCAGCACCTGAACTCCTGGGGGGACCGTCA

GTGTTCCTCTTCCCCCCAAAACCCAAGGACACCCTCATGATCTCCCGGAC

CCCTGAGGTCACATGCGTGGTGGTGGACGTGAGCCACGAAGACCCTGAGG

TCAAGTTCAACTGGTACGTGGACGGCGTGGAGGTGCATAATGCCAAGACA

AAGCCGCGGGAGGAGCAGTACAACAGCACGTACCGTGTGGTCAGCGTCCT

CACCGTCCTGCACCAGGACTGGCTGAATGGCAAGGAGTACAAGTGCAAGG

TCTCCAACAAAGCCCTCCCAGCCCCCATCGAGAAAACCATCTCCAAAGCC

AAAGGGCAGCCCCGAGAACCACAGGTGTACACCCTGCCCCCATCCCGGGA

TGAGCTGACCAAGAACCAGGTCAGCCTGACCTGCCTGGTCAAAGGCTTCT

ATCCCAGCGACATCGCCGTGGAGTGGGAGAGCAATGGGCAGCCGGAGAAC

AACTACAAGACCACGCCTCCCGTGCTGGACTCCGACGGCTCCTTCTTCCT

CTACAGCAAGCTCACCGTGGACAAGAGCAGGTGGCAGCAGGGGAACGTGT

TCTCATGCTCCGTGATGCATGAGGCTCTGCACAACCACTACACGCAGAAG

AGCCTCTCCCTGTCTCCGGGTAAAGGGGCCGCATAG

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of the present invention is embodied by the appended claims.

What is claimed is:

1. A Wnt signaling antagonist polypeptide comprising the amino acid sequence set forth in any of SEQ ID NO:1-4.

2. A Wnt signaling agonist comprising the Wnt signaling antagonist polypeptide of claim 1, linked to a binding domain having high affinity to one or both of Lrp5 and Lrp6 protein, wherein the Lrp5/6 binding domain comprises a C-terminal domain of human DKK1, or human DKK2.

3. The Wnt signaling agonist of claim 2, wherein the Lrp5/6 binding domain is joined to the Wnt signaling antagonist polypeptide through a linker.

4. The Wnt signaling agonist of claim 2, wherein the Lrp5/6 binding domain comprises C-terminal domain of human DKK2.

5. The Wnt signaling agonist of claim 2, wherein the Lrp5/6 binding domain comprises the C-terminal domain of human DKK1.

6. A Wnt signaling agonist comprising the amino acid sequence set forth in any of SEQ ID NO:5, 6, 7, 8 or 14.

7. A polynucleotide encoding the Wnt signaling agonist of claim 6.

8. The polynucleotide of claim 7, comprising the coding sequence set forth in any of SEQ ID NO:9, 10 or 15.

9. A cell culture medium, comprising an effective dose of a Wnt signaling agonist according to claim 6.

10. A method of activating or enhancing Wnt signaling, the method comprising contacting a cell expressing a frizzled receptor with an effective dose of a Wnt signaling agonist according to claim 6.

11. The method of claim 10, wherein the cell is present as a population in an in vitro culture medium.

12. The method of claim 11, wherein the cell population comprises stem cells.

13. The method of claim 11, wherein the cell population comprises organoids.

* * * * *

SEQUENCE LISTING

<160> NUMBER OF SEQ ID NOS: 18

<210> SEQ ID NO 1
<211> LENGTH: 192
<212> TYPE: PRT
<213> ORGANISM: Artificial sequence
<220> FEATURE:
<223> OTHER INFORMATION: synthetic sequence

<400> SEQUENCE: 1

Ser Glu Leu Gly Thr Arg Leu Ile Arg Ala Ala Leu Asp Gly Asn Lys

```
1               5                    10                   15
Asp Arg Val Lys Asp Leu Ile Glu Asn Gly Ala Asp Val Asn Ala Ser
                20                  25                  30

Leu Met Ser Gly Ala Thr Pro Leu His Ala Ala Met Asn Gly His
            35                  40                  45

Lys Glu Val Val Lys Leu Leu Ile Ser Lys Gly Ala Asp Val Asn Ala
        50                  55                  60

Gln Ser Val Ala Gly Ser Thr Pro Leu Asp Ala Ala Phe Ser Gly
65                  70                  75                  80

His Lys Glu Val Val Lys Leu Leu Ile Ser Lys Gly Ala Asp Val Asn
                85                  90                  95

Ala Val Asn Ala Ala Gly Leu Thr Pro Leu His Ala Ala Asp Asn
            100                 105                 110

Gly His Lys Glu Val Val Lys Leu Leu Ile Ser Lys Gly Ala Asp Val
                115                 120                 125

Asn Ala Lys Ala Asp His Gly Met Thr Pro Leu His Phe Ala Ala Gln
130                 135                 140

Arg Gly His Lys Glu Val Val Lys Leu Leu Ile Ser Lys Gly Ala Asp
145                 150                 155                 160

Leu Asn Thr Ser Ala Lys Asp Gly Ala Thr Pro Leu Asp Met Ala Arg
            165                 170                 175

Glu Ser Gly Asn Glu Glu Val Val Lys Leu Leu Glu Lys Gln Leu Glu
            180                 185                 190

<210> SEQ ID NO 2
<211> LENGTH: 192
<212> TYPE: PRT
<213> ORGANISM: Artificial sequence
<220> FEATURE:
<223> OTHER INFORMATION: synthetic sequence

<400> SEQUENCE: 2

Ser Glu Leu Gly Lys Arg Leu Ile Met Ala Ala Leu Asp Gly Asn Lys
1               5                   10                  15

Asp Arg Val Lys Asp Leu Ile Glu Asn Gly Ala Asp Val Asn Ala Ser
                20                  25                  30

Leu Val Ser Gly Ala Thr Pro Leu His Ala Ala Met Asn Gly His
            35                  40                  45

Lys Glu Val Val Lys Leu Leu Ile Ser Lys Gly Ala Asp Val Asn Ala
        50                  55                  60

Gln Ser Ala Ala Gly Ser Thr Pro Leu Ala Ala Ala Ile Asn Gly
65                  70                  75                  80

His Lys Glu Val Val Lys Leu Leu Ile Ser Lys Gly Ala Asp Val Asn
                85                  90                  95

Ala Val Thr Ala Ala Gly Met Thr Pro Leu His Ala Ala Ala Asn
            100                 105                 110

Gly His Lys Glu Val Val Lys Leu Leu Ile Ser Lys Gly Ala Asp Val
                115                 120                 125

Asn Ala Lys Ala Asp Arg Gly Met Thr Pro Leu His Phe Ala Ala Trp
130                 135                 140

Arg Gly His Lys Glu Val Val Lys Leu Leu Ile Ser Lys Gly Ala Asp
145                 150                 155                 160

Leu Asn Thr Ser Ala Lys Asp Gly Ala Thr Pro Leu Asp Met Ala Arg
            165                 170                 175

Glu Ser Gly Asn Glu Glu Val Val Lys Leu Leu Glu Lys Gln Leu Glu
```

```
<210> SEQ ID NO 3
<211> LENGTH: 192
<212> TYPE: PRT
<213> ORGANISM: Artificial sequence
<220> FEATURE:
<223> OTHER INFORMATION: synthetic sequence

<400> SEQUENCE: 3

Ser Glu Leu Gly Thr Arg Leu Ile Arg Ala Ala Leu Asp Gly Asn Lys
1               5                   10                  15

Asp Arg Val Lys Asp Leu Ile Glu Asn Gly Ala Asp Val Asn Ala Ser
            20                  25                  30

Leu Met Ser Gly Ala Thr Pro Leu His Ala Ala Met Asn Gly His
        35                  40                  45

Lys Glu Val Val Lys Leu Leu Ile Ser Lys Gly Ala Asp Val Asn Ala
    50                  55                  60

Gln Ser Val Ala Gly Ser Thr Pro Leu Asp Ala Ala Phe Ser Gly
65                  70                  75                  80

His Lys Glu Val Val Lys Leu Leu Ile Ser Lys Gly Ala Asp Val Asn
                85                  90                  95

Ala Val Asn Ala Ala Gly Leu Thr Pro Leu His Asp Ala Ala Asp Asp
            100                 105                 110

Gly His Asn Glu Val Val Lys Leu Leu Ile Ser Lys Gly Ala Asp Val
        115                 120                 125

Asn Ala Lys Ala Asp His Gly Met Thr Pro Leu His Phe Ala Ala Gln
    130                 135                 140

Arg Gly His Lys Glu Val Val Lys Leu Leu Ile Ser Lys Gly Ala Asp
145                 150                 155                 160

Leu Asn Thr Ser Ala Lys Asp Gly Ala Thr Pro Leu Asp Met Ala Arg
                165                 170                 175

Glu Ser Gly Asn Glu Glu Val Val Lys Leu Leu Glu Lys Gln Leu Glu
            180                 185                 190

<210> SEQ ID NO 4
<211> LENGTH: 192
<212> TYPE: PRT
<213> ORGANISM: Artificial sequence
<220> FEATURE:
<223> OTHER INFORMATION: synthetic sequence

<400> SEQUENCE: 4

Ser Glu Leu Gly Lys Arg Leu Ile Arg Ala Ala Leu Asp Gly Asn Lys
1               5                   10                  15

Asp Arg Val Lys Asp Leu Ile Glu Asn Gly Ala Asp Val Asn Ala Ser
            20                  25                  30

Leu Met Ser Gly Thr Thr Pro Leu Tyr Ala Ala Met Asn Gly His
        35                  40                  45

Lys Glu Val Val Lys Leu Leu Ile Ser Lys Gly Ala Asp Val Asn Ala
    50                  55                  60

Gln Ser Val Ala Gly Ser Thr Pro Leu Val Ala Ala Asn Phe Gly
65                  70                  75                  80

His Asn Glu Val Val Lys Leu Leu Ile Ser Lys Gly Ala Asp Val Asn
                85                  90                  95

Ala Val Thr Ala Phe Gly Val Thr Pro Leu His Ala Ala Ala Asp
            100                 105                 110
```

```
Gly His Lys Glu Val Val Lys Leu Leu Ile Ser Lys Gly Ala Asp Val
            115                 120                 125

Asn Ala Lys Ala Gly Arg Gly Met Thr Pro Leu His Ile Ala Ala Phe
130                 135                 140

Arg Gly His Lys Glu Val Val Lys Leu Leu Ile Ser Lys Gly Ala Asp
145                 150                 155                 160

Leu Asn Thr Ser Ala Lys Asp Gly Ala Thr Pro Leu Asp Met Ala Arg
                165                 170                 175

Glu Ser Gly Asn Glu Val Val Lys Leu Leu Glu Lys Gln Leu Glu
                180                 185                 190

<210> SEQ ID NO 5
<211> LENGTH: 292
<212> TYPE: PRT
<213> ORGANISM: Artificial sequence
<220> FEATURE:
<223> OTHER INFORMATION: synthetic sequence

<400> SEQUENCE: 5

Ser Glu Leu Gly Thr Arg Leu Ile Arg Ala Ala Leu Asp Gly Asn Lys
1               5                   10                  15

Asp Arg Val Lys Asp Leu Ile Glu Asn Gly Ala Asp Val Asn Ala Ser
                20                  25                  30

Leu Met Ser Gly Ala Thr Pro Leu His Ala Ala Ala Met Asn Gly His
            35                  40                  45

Lys Glu Val Val Lys Leu Leu Ile Ser Lys Gly Ala Asp Val Asn Ala
50                  55                  60

Gln Ser Val Ala Gly Ser Thr Pro Leu Asp Ala Ala Phe Ser Gly
65                  70                  75                  80

His Lys Glu Val Val Lys Leu Leu Ile Ser Lys Gly Ala Asp Val Asn
                85                  90                  95

Ala Val Asn Ala Ala Gly Leu Thr Pro Leu His Ala Ala Ala Asp Asn
            100                 105                 110

Gly His Lys Glu Val Val Lys Leu Leu Ile Ser Lys Gly Ala Asp Val
            115                 120                 125

Asn Ala Lys Ala Asp His Gly Met Thr Pro Leu His Phe Ala Ala Gln
130                 135                 140

Arg Gly His Lys Glu Val Val Lys Leu Leu Ile Ser Lys Gly Ala Asp
145                 150                 155                 160

Leu Asn Thr Ser Ala Lys Asp Gly Ala Thr Pro Leu Asp Met Ala Arg
                165                 170                 175

Glu Ser Gly Asn Glu Val Val Lys Leu Leu Glu Lys Gln Leu Glu
                180                 185                 190

Gly Ser Gly Ser Gly Ser Gly Ser Gly Lys Met Tyr His Thr Lys
                195                 200                 205

Gly Gln Glu Gly Ser Val Cys Leu Arg Ser Ser Asp Cys Ala Ser Gly
            210                 215                 220

Leu Cys Cys Ala Arg His Phe Trp Ser Lys Ile Cys Lys Pro Val Leu
225                 230                 235                 240

Lys Glu Gly Gln Val Cys Thr Lys His Arg Arg Lys Gly Ser His Gly
                245                 250                 255

Leu Glu Ile Phe Gln Arg Cys Tyr Cys Gly Glu Gly Leu Ser Cys Arg
            260                 265                 270

Ile Gln Lys Asp His His Gln Ala Ser Asn Ser Ser Arg Leu His Thr
            275                 280                 285
```

Cys Gln Arg His
    290

<210> SEQ ID NO 6
<211> LENGTH: 292
<212> TYPE: PRT
<213> ORGANISM: Artificial sequence
<220> FEATURE:
<223> OTHER INFORMATION: synthetic sequence

<400> SEQUENCE: 6

Ser Glu Leu Gly Lys Arg Leu Ile Met Ala Ala Leu Asp Gly Asn Lys
1               5                   10                  15

Asp Arg Val Lys Asp Leu Ile Glu Asn Gly Ala Asp Val Asn Ala Ser
            20                  25                  30

Leu Val Ser Gly Ala Thr Pro Leu His Ala Ala Ala Met Asn Gly His
        35                  40                  45

Lys Glu Val Val Lys Leu Leu Ile Ser Lys Gly Ala Asp Val Asn Ala
    50                  55                  60

Gln Ser Ala Ala Gly Ser Thr Pro Leu Ala Ala Ala Ile Asn Gly
65                  70                  75                  80

His Lys Glu Val Val Lys Leu Leu Ile Ser Lys Gly Ala Asp Val Asn
                85                  90                  95

Ala Val Thr Ala Ala Gly Met Thr Pro Leu His Ala Ala Ala Asn
            100                 105                 110

Gly His Lys Glu Val Val Lys Leu Leu Ile Ser Lys Gly Ala Asp Val
        115                 120                 125

Asn Ala Lys Ala Asp Arg Gly Met Thr Pro Leu His Phe Ala Ala Trp
130                 135                 140

Arg Gly His Lys Glu Val Val Lys Leu Leu Ile Ser Lys Gly Ala Asp
145                 150                 155                 160

Leu Asn Thr Ser Ala Lys Asp Gly Ala Thr Pro Leu Asp Met Ala Arg
                165                 170                 175

Glu Ser Gly Asn Glu Glu Val Val Lys Leu Leu Glu Lys Gln Leu Glu
            180                 185                 190

Gly Ser Gly Ser Gly Gly Ser Gly Ser Gly Lys Met Tyr His Thr Lys
        195                 200                 205

Gly Gln Glu Gly Ser Val Cys Leu Arg Ser Ser Asp Cys Ala Ser Gly
    210                 215                 220

Leu Cys Cys Ala Arg His Phe Trp Ser Lys Ile Cys Lys Pro Val Leu
225                 230                 235                 240

Lys Glu Gly Gln Val Cys Thr Lys His Arg Arg Lys Gly Ser His Gly
                245                 250                 255

Leu Glu Ile Phe Gln Arg Cys Tyr Cys Gly Glu Gly Leu Ser Cys Arg
            260                 265                 270

Ile Gln Lys Asp His His Gln Ala Ser Asn Ser Ser Arg Leu His Thr
        275                 280                 285

Cys Gln Arg His
    290

<210> SEQ ID NO 7
<211> LENGTH: 292
<212> TYPE: PRT
<213> ORGANISM: Artificial sequence
<220> FEATURE:
<223> OTHER INFORMATION: synthetic sequence

<400> SEQUENCE: 7

Ser Glu Leu Gly Thr Arg Leu Ile Arg Ala Ala Leu Asp Gly Asn Lys
1               5                   10                  15

Asp Arg Val Lys Asp Leu Ile Glu Asn Gly Ala Asp Val Asn Ala Ser
            20                  25                  30

Leu Met Ser Gly Ala Thr Pro Leu His Ala Ala Met Asn Gly His
        35                  40                  45

Lys Glu Val Val Lys Leu Leu Ile Ser Lys Gly Ala Asp Val Asn Ala
    50                  55                  60

Gln Ser Val Ala Gly Ser Thr Pro Leu Asp Ala Ala Phe Ser Gly
65                  70                  75                  80

His Lys Glu Val Val Lys Leu Leu Ile Ser Lys Gly Ala Asp Val Asn
                85                  90                  95

Ala Val Asn Ala Ala Gly Leu Thr Pro Leu His Asp Ala Ala Asp Asp
            100                 105                 110

Gly His Asn Glu Val Val Lys Leu Leu Ile Ser Lys Gly Ala Asp Val
        115                 120                 125

Asn Ala Lys Ala Asp His Gly Met Thr Pro Leu His Phe Ala Ala Gln
    130                 135                 140

Arg Gly His Lys Glu Val Val Lys Leu Leu Ile Ser Lys Gly Ala Asp
145                 150                 155                 160

Leu Asn Thr Ser Ala Lys Asp Gly Ala Thr Pro Leu Asp Met Ala Arg
            165                 170                 175

Glu Ser Gly Asn Glu Glu Val Val Lys Leu Leu Glu Lys Gln Leu Glu
            180                 185                 190

Gly Ser Gly Ser Gly Ser Gly Ser Gly Lys Met Tyr His Thr Lys
            195                 200                 205

Gly Gln Glu Gly Ser Val Cys Leu Arg Ser Ser Asp Cys Ala Ser Gly
    210                 215                 220

Leu Cys Cys Ala Arg His Phe Trp Ser Lys Ile Cys Lys Pro Val Leu
225                 230                 235                 240

Lys Glu Gly Gln Val Cys Thr Lys His Arg Arg Lys Gly Ser His Gly
                245                 250                 255

Leu Glu Ile Phe Gln Arg Cys Tyr Cys Gly Glu Gly Leu Ser Cys Arg
            260                 265                 270

Ile Gln Lys Asp His His Gln Ala Ser Asn Ser Ser Arg Leu His Thr
            275                 280                 285

Cys Gln Arg His
        290

<210> SEQ ID NO 8
<211> LENGTH: 292
<212> TYPE: PRT
<213> ORGANISM: Artificial sequence
<220> FEATURE:
<223> OTHER INFORMATION: synthetic sequence

<400> SEQUENCE: 8

Lys Met Tyr His Thr Lys Gly Gln Glu Gly Ser Val Cys Leu Arg Ser
1               5                   10                  15

Ser Asp Cys Ala Ser Gly Leu Cys Cys Ala Arg His Phe Trp Ser Lys
            20                  25                  30

Ile Cys Lys Pro Val Leu Lys Glu Gly Gln Val Cys Thr Lys His Arg
        35                  40                  45

Arg Lys Gly Ser His Gly Leu Glu Ile Phe Gln Arg Cys Tyr Cys Gly
    50                  55                  60

Glu Gly Leu Ser Cys Arg Ile Gln Lys Asp His His Gln Ala Ser Asn
 65                  70                  75                  80

Ser Ser Arg Leu His Thr Cys Gln Arg His Gly Ser Gly Ser Gly Gly
                 85                  90                  95

Ser Gly Ser Gly Ser Glu Leu Gly Lys Arg Leu Ile Arg Ala Ala Leu
            100                 105                 110

Asp Gly Asn Lys Asp Arg Val Lys Asp Leu Ile Glu Asn Gly Ala Asp
        115                 120                 125

Val Asn Ala Ser Leu Met Ser Gly Thr Thr Pro Leu Tyr Ala Ala Ala
    130                 135                 140

Met Asn Gly His Lys Glu Val Val Lys Leu Leu Ile Ser Lys Gly Ala
145                 150                 155                 160

Asp Val Asn Ala Gln Ser Val Ala Gly Ser Thr Pro Leu Val Ala Ala
                165                 170                 175

Ala Asn Phe Gly His Asn Glu Val Val Lys Leu Leu Ile Ser Lys Gly
            180                 185                 190

Ala Asp Val Asn Ala Val Thr Ala Phe Gly Val Thr Pro Leu His Ala
        195                 200                 205

Ala Ala Ala Asp Gly His Lys Glu Val Val Lys Leu Leu Ile Ser Lys
    210                 215                 220

Gly Ala Asp Val Asn Ala Lys Ala Gly Arg Gly Met Thr Pro Leu His
225                 230                 235                 240

Ile Ala Ala Phe Arg Gly His Lys Glu Val Val Lys Leu Leu Ile Ser
                245                 250                 255

Lys Gly Ala Asp Leu Asn Thr Ser Ala Lys Asp Gly Ala Thr Pro Leu
            260                 265                 270

Asp Met Ala Arg Glu Ser Gly Asn Glu Glu Val Val Lys Leu Leu Glu
        275                 280                 285

Lys Gln Leu Glu
    290

<210> SEQ ID NO 9
<211> LENGTH: 890
<212> TYPE: DNA
<213> ORGANISM: Artificial sequence
<220> FEATURE:
<223> OTHER INFORMATION: synthetic sequence

<400> SEQUENCE: 9
ggatcctctg aactgggtac gcgtctgatc agggcagcat tagacggtaa caaagaccgt    60
gttaaagacc tcattgaaaa tggtgctgac gttaacgcgt cccttatgtc tggggcgact   120
ccgttacacg ccgccgccat gaacggccac aaagaggttg tgaagttact gatctccaag   180
ggcgcagatg tgaatgctca gtccgttgcg ggttctacac tctggatgc ggcggcgttt    240 agtggacata aagaagtggt aaaactgctg ataagtaaag gagcagacgt caatgctgtt   300
aatgcggctg gattgacccc cctacatgct gctgctgata tgggcacaa ggaagtagtg    360 aagttgctta tttctaaggg ggccgacgta aatgcgaaag ctgaccatgg catgactcca   420
ctccatttcg cagcacagcg cggtcataag gaagtcgtta actattaat cagcaaaggt    480 gcggatttga acacctctgc caaagacggt gcaaccccgc ttgacatggc gcgtgaatct   540
ggcaatgagg aggttgtcaa gctcttggaa aagcaactcg agggaagcgg ttccggaggt   600
tctggctccg gaaaaatgta tcacactaag ggacaggaag cagcgtgtg cctgaggtcc    660 tctgactgtg catctggcct gtgctgcgcc agacactttt ggtccaaaat ctgcaagccg   720

| | |
|---|---|
| gttctgaaag agggccaggt gtgcacaaag catcgacgaa agggcagcca tggactcgag | 780 |
| atctttcaga ggtgctactg cggggagggt ctgtcttgca gaatccagaa agatcatcat | 840 |
| caggcctcca actcctcccg cctgcacacc tgccagcgac atgcggccgc | 890 |

<210> SEQ ID NO 10
<211> LENGTH: 890
<212> TYPE: DNA
<213> ORGANISM: Artificial sequence
<220> FEATURE:
<223> OTHER INFORMATION: synthetic sequence

<400> SEQUENCE: 10

| | |
|---|---|
| ggatccagcg aactcggcac ccgacttatc agagctgccc ttgatggaaa taaggaccgg | 60 |
| gtcaaagacc tgatagagaa tggggcggac gttaatgcaa gtcttatgtc cggtgctacc | 120 |
| ccgttgcatg ccgctgcaat gaatggccac aaggaggttg taaaattgct cataagtaaa | 180 |
| ggcgcagaca taaacgcaca atccgtggcg ggcagtaccc ccttggatgc cgctgcgttc | 240 |
| tcaggccata agaggtcgt aaaactgctg atctccaaag gagcggacgt caatgcagta | 300 |
| aatgctgcag gacttacccc cttgcacgcc gctgccgaca atggacacaa ggaggttgta | 360 |
| aaacttctca tatctaaagg cgcggacgtc aacgctaaag cggaccacgg aatgacgccg | 420 |
| ctccactttg cggcacagag gggccataaa gaggtagtga acttctgat ctcaaaagga | 480 |
| gccgacttga atacgagcgc taaggatggt gcaacgccat ggatatggc cagggagtcc | 540 |
| ggaaatgaag aggtggtgaa gctgcttgag aagcaactcg aaggtagcgg gagcggcggg | 600 |
| agtggctctg gcaagatgta ccataccaag ggccaagaag ggagtgtgtg cctgcggtca | 660 |
| agcgactgcg catcaggctt gtgctgtgct aggcatttct ggtccaagat ttgtaagcca | 720 |
| gtattgaagg aaggccaggt gtgtactaaa cataggcgca agggaagtca tggtctcgag | 780 |
| atattccaac gctgttactg tggcgaggga ttgtcttgcc gcatacaaaa agaccaccac | 840 |
| caggcgtcta actctagtag gcttcacaca tgccaacggc acgcggccgc | 890 |

<210> SEQ ID NO 11
<211> LENGTH: 993
<212> TYPE: DNA
<213> ORGANISM: Artificial sequence
<220> FEATURE:
<223> OTHER INFORMATION: synthetic sequence

<400> SEQUENCE: 11

| | |
|---|---|
| gctagcacca agggcccatc ggtcttcccc ctggcaccct cctccaagag cacctctggg | 60 |
| ggcacagcgg ccctgggctg cctggtcaag gactacttcc ccgaaccggt gacggtgtcg | 120 |
| tggaactcag gcgccctgac cagcggcgtg cacaccttcc cggctgtcct acagtcctca | 180 |
| ggactctact ccctcagcag cgtggtgacc gtgccctcca gcagcttggg cacccagacc | 240 |
| tacatctgca acgtgaatca caagcccagc aacaccaagg tggacaagaa agttgagccc | 300 |
| aaatcttgtg acaaaactca cacatgccca ccgtgcccag cacctgaact cctggggga | 360 |
| ccgtcagtct tcctcttccc cccaaaaccc aaggacaccc tcatgatctc ccggacccct | 420 |
| gaggtcacat gcgtggtggt ggacgtgagc cacgaagacc ctgaggtcaa gttcaactgg | 480 |
| tacgtggacg gcgtggaggt gcataatgcc aagacaaagc cgcgggagga gcagtacaac | 540 |
| agcacgtacc gtgtggtcag cgtcctcacc gtcctgcacc aggactggct gaatggcaag | 600 |
| gagtacaagt gcaaggtctc caacaaagcc ctcccagccc ccatcgagaa aaccatctcc | 660 |

```
aaagccaaag ggcagccccg agaaccacag gtgtacaccc tgcccccatc ccgggaggag    720
atgaccaaga accaggtcag cctgacctgc ctggtcaaag gcttctatcc cagcgacatc    780
gccgtggagt gggagagcaa tgggcagccg gagaacaact acaagaccac gcctcccgtg    840
ctggactccg acggctcctt cttcctctac agcaagctca ccgtggacaa gagcaggtgg    900 cagcaggga acgtcttctc atgctccgtg atgcatgagg ctctgcacaa ccactacacg    960
cagaagagcc tctccctgtc tccgggtaaa tga                                 993
```

```
<210> SEQ ID NO 12
<211> LENGTH: 90
<212> TYPE: PRT
<213> ORGANISM: Artificial sequence
<220> FEATURE:
<223> OTHER INFORMATION: synthetic sequence

<400> SEQUENCE: 12

Lys Met Tyr His Thr Lys Gly Gln Glu Gly Ser Val Cys Leu Arg Ser
1               5                   10                  15

Ser Asp Cys Ala Ser Gly Leu Cys Cys Ala Arg His Phe Trp Ser Lys
            20                  25                  30

Ile Cys Lys Pro Val Leu Lys Glu Gly Gln Val Cys Thr Lys His Arg
        35                  40                  45

Arg Lys Gly Ser His Gly Leu Glu Ile Phe Gln Arg Cys Tyr Cys Gly
    50                  55                  60

Glu Gly Leu Ser Cys Arg Ile Gln Lys Asp His His Gln Ala Ser Asn
65                  70                  75                  80

Ser Ser Arg Leu His Thr Cys Gln Arg His
                85                  90

<210> SEQ ID NO 13
<211> LENGTH: 88
<212> TYPE: PRT
<213> ORGANISM: Artificial sequence
<220> FEATURE:
<223> OTHER INFORMATION: synthetic sequence

<400> SEQUENCE: 13

Lys Met Ser His Ile Lys Gly His Glu Gly Asp Pro Cys Leu Arg Ser
1               5                   10                  15

Ser Asp Cys Ile Glu Gly Phe Cys Cys Ala Arg His Phe Trp Thr Lys
            20                  25                  30

Ile Cys Lys Pro Val Leu His Gln Gly Glu Val Cys Thr Lys Gln Arg
        35                  40                  45

Lys Lys Gly Ser His Gly Leu Glu Ile Phe Gln Arg Cys Asp Cys Ala
    50                  55                  60

Lys Gly Leu Ser Cys Lys Val Trp Lys Asp Ala Thr Tyr Ser Ser Lys
65                  70                  75                  80

Ala Arg Leu His Val Cys Gln Lys
                85

<210> SEQ ID NO 14
<211> LENGTH: 561
<212> TYPE: PRT
<213> ORGANISM: Artificial sequence
<220> FEATURE:
<223> OTHER INFORMATION: synthetic sequence

<400> SEQUENCE: 14

Met Ala Arg Pro Leu Cys Thr Leu Leu Leu Leu Met Ala Thr Leu Ala
```

```
1               5                   10                  15
Gly Ala Leu Ala Gly Ser Ser Glu Leu Gly Thr Arg Leu Ile Arg Ala
            20                  25                  30
Ala Leu Asp Gly Asn Lys Asp Arg Val Lys Asp Leu Ile Glu Asn Gly
            35                  40                  45
Ala Asp Val Asn Ala Ser Leu Met Ser Gly Ala Thr Pro Leu His Ala
    50                  55                  60
Ala Ala Met Asn Gly His Lys Glu Val Val Lys Leu Leu Ile Ser Lys
65                  70                  75                  80
Gly Ala Asp Val Asn Ala Gln Ser Val Ala Gly Ser Thr Pro Leu Asp
                85                  90                  95
Ala Ala Ala Phe Ser Gly His Lys Glu Val Val Lys Leu Leu Ile Ser
            100                 105                 110
Lys Gly Ala Asp Val Asn Ala Val Asn Ala Ala Gly Leu Thr Pro Leu
            115                 120                 125
His Ala Ala Ala Asp Asn Gly His Lys Glu Val Val Lys Leu Leu Ile
        130                 135                 140
Ser Lys Gly Ala Asp Val Asn Ala Lys Ala Asp His Gly Met Thr Pro
145                 150                 155                 160
Leu His Phe Ala Ala Gln Arg Gly His Lys Glu Val Val Lys Leu Leu
            165                 170                 175
Ile Ser Lys Gly Ala Asp Leu Asn Thr Ser Ala Lys Asp Gly Ala Thr
            180                 185                 190
Pro Leu Asp Met Ala Arg Glu Ser Gly Asn Glu Glu Val Val Lys Leu
            195                 200                 205
Leu Glu Lys Gln Leu Glu Gly Ser Gly Ser Gly Ser Gly Ser Gly Gly
        210                 215                 220
Lys Met Tyr His Thr Lys Gly Gln Glu Gly Ser Val Cys Leu Arg Ser
225                 230                 235                 240
Ser Asp Cys Ala Ser Gly Leu Cys Cys Ala Arg His Phe Trp Ser Lys
            245                 250                 255
Ile Cys Lys Pro Val Leu Lys Glu Gly Gln Val Cys Thr Lys His Arg
            260                 265                 270
Arg Lys Gly Ser His Gly Leu Glu Ile Phe Gln Arg Cys Tyr Cys Gly
        275                 280                 285
Glu Gly Leu Ser Cys Arg Ile Gln Lys Asp His His Gln Ala Ser Asn
        290                 295                 300
Ser Ser Arg Leu His Thr Cys Gln Arg His Ala Ala Ala Glu Asn Leu
305                 310                 315                 320
Tyr Phe Gln Gly Ser Ser Glu Pro Lys Ser Cys Asp Lys Thr His Thr
            325                 330                 335
Cys Pro Pro Cys Pro Ala Pro Glu Leu Leu Gly Gly Pro Ser Val Phe
        340                 345                 350
Leu Phe Pro Pro Lys Pro Lys Asp Thr Leu Met Ile Ser Arg Thr Pro
        355                 360                 365
Glu Val Thr Cys Val Val Val Asp Val Ser His Glu Asp Pro Glu Val
    370                 375                 380
Lys Phe Asn Trp Tyr Val Asp Gly Val Glu Val His Asn Ala Lys Thr
385                 390                 395                 400
Lys Pro Arg Glu Glu Gln Tyr Asn Ser Thr Tyr Arg Val Val Ser Val
            405                 410                 415
Leu Thr Val Leu His Gln Asp Trp Leu Asn Gly Lys Glu Tyr Lys Cys
            420                 425                 430
```

Lys Val Ser Asn Lys Ala Leu Pro Ala Pro Ile Glu Lys Thr Ile Ser
            435                 440                 445

Lys Ala Lys Gly Gln Pro Arg Glu Pro Gln Val Tyr Thr Leu Pro Pro
        450                 455                 460

Ser Arg Asp Glu Leu Thr Lys Asn Gln Val Ser Leu Thr Cys Leu Val
465                 470                 475                 480

Lys Gly Phe Tyr Pro Ser Asp Ile Ala Val Glu Trp Glu Ser Asn Gly
                485                 490                 495

Gln Pro Glu Asn Asn Tyr Lys Thr Thr Pro Pro Val Leu Asp Ser Asp
            500                 505                 510

Gly Ser Phe Phe Leu Tyr Ser Lys Leu Thr Val Asp Lys Ser Arg Trp
        515                 520                 525

Gln Gln Gly Asn Val Phe Ser Cys Ser Val Met His Glu Ala Leu His
530                 535                 540

Asn His Tyr Thr Gln Lys Ser Leu Ser Leu Ser Pro Gly Lys Gly Ala
545                 550                 555                 560

Ala

<210> SEQ ID NO 15
<211> LENGTH: 1686
<212> TYPE: DNA
<213> ORGANISM: Artificial sequence
<220> FEATURE:
<223> OTHER INFORMATION: synthetic sequence

<400> SEQUENCE: 15
atggcccggc tctgtgtac cctgctactc ctgatggcta ccctggctgg ggctctggcc        60
ggatccagcg aactcggcac ccgacttatc agagctgccc ttgatggaaa taaggaccgg      120
gtcaaagacc tgatagagaa tggggcggac gttaatgcaa gtcttatgtc cggtgctacc      180
ccgttgcatg ccgctgcaat gatggccac aaggaggttg taaaattgct cataagtaaa      240
ggcgcagacg taaacgcaca atccgtggcg ggcagtaccc ccttggatgc cgctgcgttc      300
tcaggccata agaggtcgt aaaactgctg atctccaaag gagcggacgt caatgcagta      360
aatgctgcag gacttacccc cttgcacgcc gctgccgaca tggacacaa ggaggttgta      420 aaacttctca tatctaaagg cgcggacgtc aacgctaaag cggaccacgg aatgacgccg      480
ctccactttg cggcacagag gggccataaa gaggtagtga acttctgat ctcaaaagga      540 gccgacttga atacgagcgc taaggatggt gcaacgccat ggatatggc agggagtcc      600 ggaaatgaag aggtggtgaa gctgcttgag aagcaactcg aaggtagcgg gagcggcggg      660
agtggctctg gcaagatgta ccataccaag ggccaagaag ggagtgtgtg cctgcggtca      720
agcgactgcg catcaggctt gtgctgtgct aggcatttct ggtccaagat ttgtaagcca      780
gtattgaagg aaggccaggt gtgtactaaa cataggcgca agggaagtca tggtctcgag      840
atattccaac gctgttactg tggcgaggga ttgtcttgcc gcatacaaaa agaccaccac      900
caggcgtcta actctagtag gcttcacaca tgccaacggc acgcggccgc agagaacctg      960
tacttccagg gatcttccga gcccaaatct tgtgacaaaa ctcacacatg cccaccgtgc     1020
ccagcacctg aactcctggg gggaccgtca gtcttcctct ccccccaaa acccaaggac     1080 accctcatga tctcccggac ccctgaggtc acatgcgtgg tggtggacgt gagccacgaa     1140
gaccctgagg tcaagttcaa ctggtacgtg gacggcgtgg aggtgcataa tgccaagaca     1200
aagccgcggg aggagcagta caacagcacg taccgtgtgg tcagcgtcct caccgtcctg     1260

-continued

```
caccaggact ggctgaatgg caaggagtac aagtgcaagg tctccaacaa agccctccca    1320
gcccccatcg agaaaaccat ctccaaagcc aagggcagc cccgagaacc acaggtgtac     1380
accctgcccc catcccggga tgagctgacc aagaaccagg tcagcctgac ctgcctggtc    1440
aaaggcttct atcccagcga catcgccgtg gagtgggaga gcaatgggca gccggagaac    1500
aactacaaga ccacgcctcc cgtgctggac tccgacggct ccttcttcct ctacagcaag    1560
ctcaccgtgg acaagagcag gtggcagcag gggaacgtct tctcatgctc cgtgatgcat    1620
gaggctctgc acaaccacta cacgcagaag agcctctccc tgtctccggg taaaggggcc    1680
gcatag                                                                1686
```

<210> SEQ ID NO 16
<211> LENGTH: 20
<212> TYPE: PRT
<213> ORGANISM: Artificial sequence
<220> FEATURE:
<223> OTHER INFORMATION: synthetic sequence

<400> SEQUENCE: 16

Met Ala Arg Pro Leu Cys Thr Leu Leu Leu Met Ala Thr Leu Ala
1               5                   10                  15

Gly Ala Leu Ala
            20

<210> SEQ ID NO 17
<211> LENGTH: 8
<212> TYPE: PRT
<213> ORGANISM: Artificial sequence
<220> FEATURE:
<223> OTHER INFORMATION: synthetic sequence

<400> SEQUENCE: 17

Glu Asn Leu Tyr Phe Gln Gly Ser
1               5

<210> SEQ ID NO 18
<211> LENGTH: 236
<212> TYPE: PRT
<213> ORGANISM: Artificial sequence
<220> FEATURE:
<223> OTHER INFORMATION: synthetic sequence

<400> SEQUENCE: 18

Ser Glu Pro Lys Ser Cys Asp Lys Thr His Thr Cys Pro Pro Cys Pro
1               5                   10                  15

Ala Pro Glu Leu Leu Gly Gly Pro Ser Val Phe Leu Phe Pro Pro Lys
                20                  25                  30

Pro Lys Asp Thr Leu Met Ile Ser Arg Thr Pro Glu Val Thr Cys Val
            35                  40                  45

Val Val Asp Val Ser His Glu Asp Pro Glu Val Lys Phe Asn Trp Tyr
        50                  55                  60

Val Asp Gly Val Glu Val His Asn Ala Lys Thr Lys Pro Arg Glu Glu
65                  70                  75                  80

Gln Tyr Asn Ser Thr Tyr Arg Val Val Ser Val Leu Thr Val Leu His
                85                  90                  95

Gln Asp Trp Leu Asn Gly Lys Glu Tyr Lys Cys Lys Val Ser Asn Lys
            100                 105                 110

Ala Leu Pro Ala Pro Ile Glu Lys Thr Ile Ser Lys Ala Lys Gly Gln
        115                 120                 125

```
Pro Arg Glu Pro Gln Val Tyr Thr Leu Pro Pro Ser Arg Asp Glu Leu
    130                 135             140

Thr Lys Asn Gln Val Ser Leu Thr Cys Leu Val Lys Gly Phe Tyr Pro
145                 150             155                     160

Ser Asp Ile Ala Val Glu Trp Glu Ser Asn Gly Gln Pro Glu Asn Asn
                165             170             175

Tyr Lys Thr Thr Pro Pro Val Leu Asp Ser Asp Gly Ser Phe Phe Leu
            180             185             190

Tyr Ser Lys Leu Thr Val Asp Lys Ser Arg Trp Gln Gln Gly Asn Val
        195             200             205

Phe Ser Cys Ser Val Met His Glu Ala Leu His Asn His Tyr Thr Gln
    210             215             220

Lys Ser Leu Ser Leu Ser Pro Gly Lys Gly Ala Ala
225             230             235
```